US010975397B2

(12) United States Patent
Ogawa et al.

(10) Patent No.: US 10,975,397 B2
(45) Date of Patent: Apr. 13, 2021

(54) METHOD FOR PRODUCING OXO FATTY ACID AND RARE FATTY ACID

(71) Applicants: KYOTO UNIVERSITY, Kyoto (JP); Noster Inc., Muko (JP)

(72) Inventors: Jun Ogawa, Kyoto (JP); Shigenobu Kishino, Kyoto (JP); Sakayu Shimizu, Kyoto (JP); Yasunori Yonejima, Muko (JP)

(73) Assignees: KYOTO UNIVERSITY, Kyoto (JP); Noster Inc., Muko (JP)

( * ) Notice: Subject to any disclaimer, the term of this patent is extended or adjusted under 35 U.S.C. 154(b) by 0 days.

(21) Appl. No.: 16/369,271

(22) Filed: Mar. 29, 2019

(65) Prior Publication Data
US 2019/0218579 A1    Jul. 18, 2019

Related U.S. Application Data

(62) Division of application No. 15/629,716, filed on Jun. 21, 2017, now Pat. No. 10,294,501, which is a division of application No. 14/400,116, filed as application No. PCT/JP2012/078747 on Nov. 6, 2012, now Pat. No. 9,719,115.

(30) Foreign Application Priority Data

May 10, 2012    (JP) ................. 2012-108928

(51) Int. Cl.
    *C12P 7/64*   (2006.01)
    *C12R 1/25*   (2006.01)
(52) U.S. Cl.
    CPC ............ *C12P 7/6409* (2013.01); *C12P 7/64* (2013.01); *C12P 7/6427* (2013.01); *C12R 1/25* (2013.01)
(58) Field of Classification Search
    None
    See application file for complete search history.

(56) References Cited

U.S. PATENT DOCUMENTS

| 5,246,841 A | 9/1993 | Yazawa et al. |
| 6,184,009 B1 | 2/2001 | Cain et al. |
| 2008/0057044 A1 | 3/2008 | Lee et al. |
| 2010/0069492 A1 | 3/2010 | Geiringen et al. |
| 2012/0302777 A1 | 11/2012 | Ochiai |

FOREIGN PATENT DOCUMENTS

| JP | S48-081810 A | 11/1973 |
| JP | S58-165795 A | 9/1983 |
| JP | H07-289241 A | 11/1995 |
| JP | 2002-017381 A | 1/2002 |
| JP | 2007-138181 A | 6/2007 |
| JP | 2007-252333 A | 10/2007 |
| JP | 2007-259712 A | 10/2007 |
| JP | 2008-511312 A | 4/2008 |
| JP | 2009-197195 A | 9/2009 |
| JP | 2009-542205 A | 12/2009 |
| JP | 2011-184411 A | 9/2011 |
| WO | 2011/096481 A1 | 8/2011 |

OTHER PUBLICATIONS

GenBank Accession No. NC_004567.1. "Lactobacillus plantatrum WCFS1, complete genome" (Year: 2011).*
Demir et al., "Chemoenzymatic Conversion of Linoleic Acid into Conjugated Linoleic Acid," *J. Agrlc. Food Chem.*, 58: 1646-1652 (2010).
Genbank, "Lactobacillus plantarum JDM1," Accession No. CP001617 (Jul. 2009).
Ha et al., "Anticarcinogens from fried ground beef: heat-altered derivatives of linoleic acid," *Carcinogenesis*, 8(12): 1881-1887 (1987).
Hou, Ching, "Production of Hydroxy Fatty Acids from Unsaturated Fatty Acids by *Flavobacterium* sp SD5 Hydratase, a C-10 Positional- and cis Unsaturation-Specific Enzyme", *JAOCS*, 72(11): 1265-1270 (1955).
Ip et al., "Mammary Cancer Prevention by Conjugated Dienoic Derivative of Linoleic Acid," *Cancer Research*, 51: 6118-6124 (1991).
Kim et al., "9-oxo-10(E),12(E)-octadecadienoic acid derived from tomato is a potent PPAR α agonist to decrease triglyceride accumulation in mouse primary hepatocytes," *Mol. Nutr. Food Res.*, 55: 585-593 (2011).
Kim et al., "Potent PPARα Activator Derived from Tomato Juice, 13-oxo-9,11-Octadecadienoic Acid, Decreases Plasma and Hepatic Triglyceride in Obese Diabetic Mice," *PLoS One*, 7(2): e31317 (Feb. 2012).
Kishino, "Biseibutsu o Mochiita Sentakuteki na Kinosei Shishitsu Seisanho no Kakuritsu" [Abstract of Technical Report of Industrial Technology Research Grant Program in FY2010—"Establishment of Selective Production Method of Functional Lipids by Using Microorganism" (Project ID 07A08005a)], New Energy and Industrial Technology Development Organization (NEDO), Heisei 22 Nendo Sangyo Gijutsu Kenkyu Josei Jigyo Kenkyu Seika Hokokusho (Saishu) (Apr. 26, 2012).

(Continued)

*Primary Examiner* — Rebecca E Prouty
(74) *Attorney, Agent, or Firm* — Leydig, Voit & Mayer, Ltd.

(57) ABSTRACT

The present invention provides a production method of oxo fatty acid, as well as rare fatty acids such as conjugated fatty acid, hydroxylated fatty acid, partially saturated fatty acid and the like, which uses 4 kinds of enzymes (fatty acid-hydratase, hydroxylated fatty acid-dehydrogenase, oxo fatty acid-isomerase, oxo fatty acid-enone reductase) derived from *Lactobacillus plantarum* including lactic acid bacteria and the like. Furthermore, the present invention also provides a more efficient production method of oxo fatty acid and the like, which partly uses a chemical oxidation reaction in combination.

8 Claims, 1 Drawing Sheet
Specification includes a Sequence Listing.

(56) References Cited

OTHER PUBLICATIONS

Kishino et al., "Novel multi-component enzyme machinery in lactic acid bacteria catalyzing C=C double bond migration useful for conjugated fatty acid synthesis," *Biochemical and Biophysical Research Communications*, 416: 188-193 (2011).
Kishino et al., "Discovery of the key enzyme for the saturation of unsaturated fatty acids in the lactic acid bacteria," *Nendo Taikai Koen Yoshishu* [Proceedings of the Annual Meeting in 2012 of the Japan Society for Bioscience, Biotechnology, and Agrochemistry], Item 3C23a11 (Mar. 5, 2012).
Lee et al., "Conjugated linoleic acid and atherosclerosis in rabbits," *Atherosclerosis*, 108: 19-25 (1994).
NCBI, "nitroreductase [Lactobacillus plantarum JDM1]," Reference Sequence No. YP_003061658.1 (Jul. 2009).
Ogawa et al., "Production of Conjugated Fatty Acids by Lactic Acid Bacteria," *Journal of Bioscience and Bioengineering*, 100(4): 355-364 (2005).
Ogawa et al., "Chonai Saikin ni Tokui na Shishitsu Taisha 'Shibosan Howaka Hanno' ni Kan'yo suru Shinki Kosokei no Kino Kaiseki to Oyo", *Journal of Japan Foundation of Applied Enzymology*, 46: 13-21 (2012).
Sigma-Aldrich Japan, "Fatty Acid/FAME Application Guide—Analysis of Foods for Nutritional Needs," pp. 3-4, 24 (2010).
Japanese Patent Office, International Search Report in International Patent Application No. PCT/JP2012/078747 (dated Feb. 12, 2013).
Japanese Patent Office, Notice of Reasons for Refusal in Japanese Patent Application No. 2014-514349 (dated Sep. 20, 2016).
Japanese Patent Office, Decision of Dismissal of Amendment in Japanese Patent Application No. 2014-514349 (dated Nov. 14, 2017).
U.S. Appl. No. 14/400,116, filed Nov. 10, 2014.
U.S. Appl. No. 15/629,716, filed Jun. 21, 2017.
Crameri et al., "DNA shuffling of a family of genes from diverse species accelerates directed evolution," *Nature*, 391(6664): 288-291 (1998).

\* cited by examiner

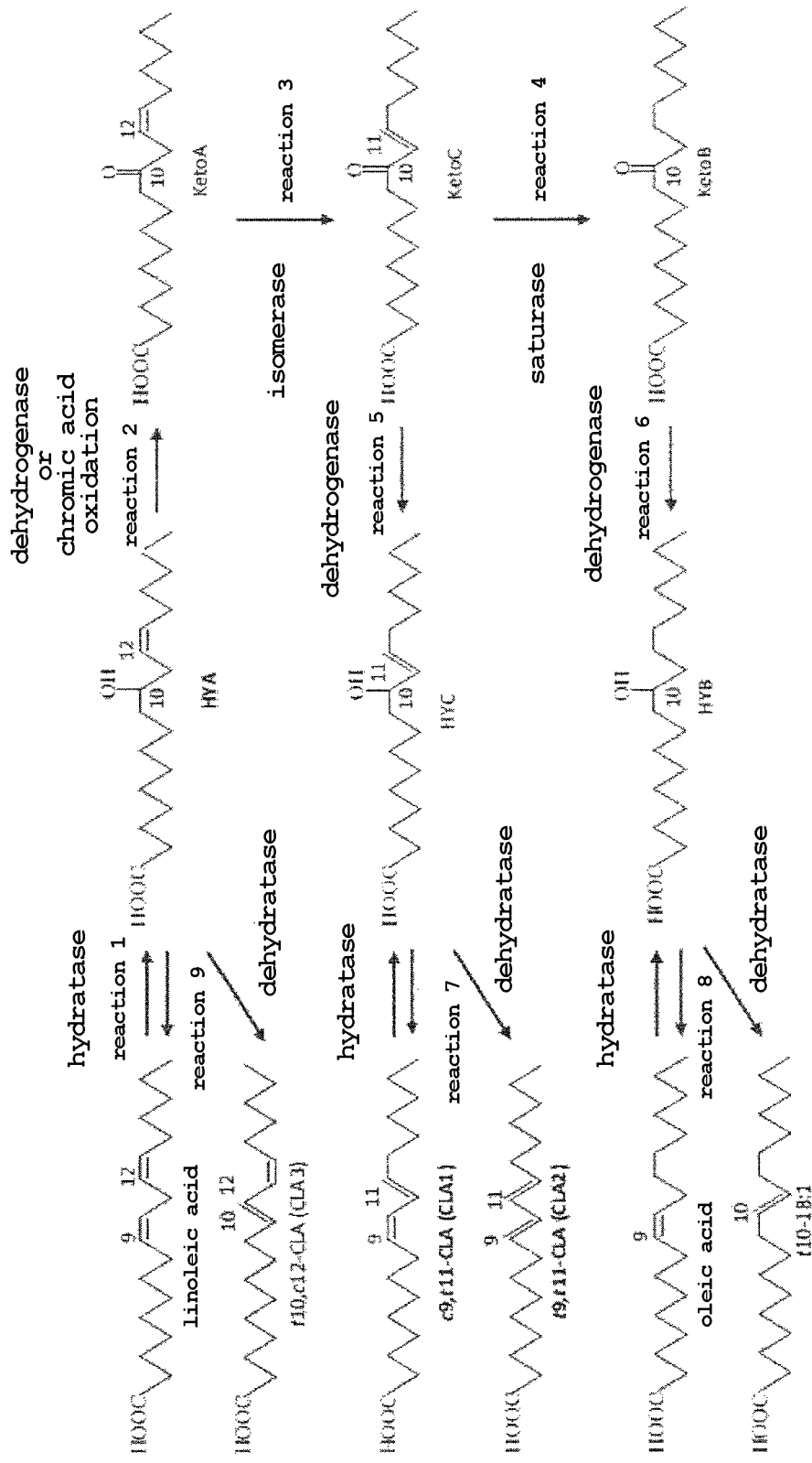

METHOD FOR PRODUCING OXO FATTY ACID AND RARE FATTY ACID

CROSS-REFERENCE TO RELATED APPLICATIONS

This patent application is a divisional of copending U.S. patent application Ser. No. 15/629,716, filed on Jun. 21 2017, now U.S. Pat. No. 10,294,501, which is divisional of U.S. patent application Ser. No. 14/400,116, filed on Nov. 10, 2014, now U.S. Pat. No. 9,719,115, which is the U.S. national phase of International Patent Application No. PCT/JP2012/078747, filed Nov. 6, 2012, which claims the benefit of Japanese Patent Application No. 2012-108928, filed on May 10, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 6,314 bytes ASCII (Text) file named "742355SequenceListing.txt," created Mar. 26, 2019.

TECHNICAL FIELD

The present invention relates to a production method of a fatty acid. More detailedly, the present invention relates to a production method of an oxo fatty acid, comprising using an unsaturated fatty acid as a starting material and multi-step enzyme reaction or combining a chemical oxidation reaction and an enzyme reaction method, and a production method of a rare fatty acid from an oxo fatty acid.

BACKGROUND ART

Conjugated fatty acid represented by conjugated linoleic acid (CLA) has been reported to have various physiological activities such as a lipid metabolism improving effect, an anti-arteriosclerosis action, a body fats decreasing action and the like (non-patent documents 1-3), and is a functional lipid expected to be applicable to various fields of medicament, functional food and the like (patent documents 1, 2). While CLA is known to be contained in dairy products and meat products since it is produced by microorganisms present in the stomach of ruminant and to be present in a small amount in vegetable oil, the detailed mechanism of production thereof is not known.

The present inventors reported that 3 kinds of enzymes present in the fungus body of *Lactobacillus plantarum* (CLA-HY, CLA-DC, CLA-DH) are essential for the reaction to convert linoleic acid to conjugated linoleic acid (patent document 1). However, the mechanism of a series of specific reactions, the presence of an intermediate and the like in these enzyme reactions have not been clarified.

In addition, it has been reported in recent years that oxo fatty acids such as 9-oxo-octadecadienoic acid, 13-oxo-octadecadienoic acid and the like contained in tomato have an activity to improve lifestyle-related diseases, such as lipid metabolism improvement and the like (patent document 3, non-patent documents 4, 5), and the physiological activity of oxo fatty acid is drawing attention. While oxo fatty acid has a carbonyl group at a particular position of unsaturated fatty acid, synthesis of functional oxo fatty acid from unsaturated fatty acid is difficult since it is necessary to distinguish double bonds present in a plurality in a molecule and introduce carbonyl group into a particular position. Also, it is not known that rare fatty acids such as CLA1, CLA2 and the like are produced from a particular oxo fatty acid.

DOCUMENT LIST

Patent Documents patent document 1: JP-A-2007-259712
patent document 2: JP-A-2007-252333
patent document 3: JP-A-2011-184411

Non-Patent Documents non-patent document 1: Ha Y L, (1987), Carcinogenesis, vol. 8, no. 12, p. 1881-1887
non-patent document 2: Clement Ip, (1991), Cancer Res., (1991), vol. 51, p. 6118-6124
non-patent document 3: Kisun N L, (1994), Atherosclerosis, vol. 108, p. 19-25
non-patent document 4: Kim Y-I, (2011), Mol. Nutr. Food Res., vol. 55, p. 585-593
non-patent document 5: Kim Y-I, (2012), PLoS ONE, vol. 7, no. 2, e31317

SUMMARY OF THE INVENTION

Problems to be Solved by the Invention

An object of the present invention is to provide a method of efficiently producing an oxo fatty acid, and a method of producing a rare fatty acid such as hydroxylated fatty acid, conjugated fatty acid, partially saturated fatty acid and the like from the produced oxo fatty acid.

Means of Solving the Problems

The present inventors have clarified the full particulars of the unsaturated fatty acid metabolic pathway of lactic acid bacteria, found oxo fatty acid, hydroxylated fatty acid, conjugated fatty acid and partially saturated fatty acid as intermediates for the metabolic system, and identified a novel enzyme (CLA-ER) involved in the production of them.

To be specific, using known enzymes (CLA-HY, CLA-DC, CLA-DH) and a novel enzyme (CLA-ER), the present inventors have clarified a series of mechanisms of the production of cis-9, trans-11-conjugated linoleic acid (c9, t11-CLA (CLA1)), trans-9, trans-11-conjugated linoleic acid (t9,t11-CLA (CLA2)), oleic acid, trans-10-octadecenoic acid (t10-18:1) and the like from linoleic acid (see FIGURE). They have also found that oxo fatty acids such as 10-oxo-cis-12-octadecenoic acid (hereinafter to be also referred to as "KetoA"), 10-oxooctadecanoic acid (hereinafter to be also referred to as "KetoB"), 10-oxo-trans-11-octadecenoic acid (hereinafter to be also referred to as "KetoC") and the like are produced as intermediates for the reaction, and further that the conversion efficiency is remarkably improved by introducing a chemical oxidation method using chromic acid instead of a part of enzyme reactions (oxidation reaction of hydroxylated fatty acid).

In addition, the present inventors have also found that, using oxo fatty acid, large supply of which has been achieved for the first time by the present invention as a starting material, rare fatty acids such as hydroxylated fatty acid, conjugated fatty acid and partially saturated fatty acid can be produced by a conventionally-unknown reaction pathway of Keto C from Keto A, Keto B from Keto C, 10-hydroxy-trans-11-octadecenoic acid from Keto C (hereinafter to be also referred to as "HYC"), 10-hydroxy-octadecanoic acid from Keto B (hereinafter to be also referred to as "HYB"), CLA1 or CLA2 from HYC, oleic acid or trans-10-octadecenoic acid from HYB, and linoleic acid or trans-10,cis-12-conjugated linoleic acid (t10, c12-CLA (CLA3)) from 10-hydroxy-cis-12-octadecenoic acid (hereinafter to be also referred to as "HYA"). The present invention was completed based on the above findings.

Accordingly, the present invention provides the following:

[1] A method of producing an oxo fatty acid having 18 carbon atoms and a carbonyl group at the 10-position, comprising inducing a hydroxylated fatty acid having 18 carbon atoms and a hydroxyl group at the 10-position from an unsaturated fatty acid having 18 carbon atoms and a cis-type double bond at the 9-position by a hydratase reaction, and subjecting the hydroxylated fatty acid to a dehydrogenase reaction or chemical oxidation.

[2] The method of [1], wherein the unsaturated fatty acid having 18 carbon atoms and a cis-type double bond at the 9-position is oleic acid, linoleic acid, γ-linolenic acid, α-linolenic acid, stearidonic acid, cis-9,trans-11-octadecadienoic acid or ricinoleic acid.

[3] The method of [1] or [2], wherein the hydratase and the dehydrogenase are derived from lactic acid bacteria.

[4] The method of [3], wherein the lactic acid bacteria is Lactobacillus plantarum FERM BP-10549 strain.

[5] A method of producing an oxo fatty acid having 18 carbon atoms, a carbonyl group at the 10-position and a trans-type double bond at the 11-position from an oxo fatty acid having 18 carbon atoms, a carbonyl group at the 10-position and a cis-type double bond at the 12-position, by an isomerase reaction.

[6] The method of [5], wherein the oxo fatty acid having 18 carbon atoms, a carbonyl group at the 10-position and a cis-type double bond at the 12-position is 10-oxo-cis-12-octadecenoic acid, 10-oxo-cis-6,cis-12-octadecadienoic acid, 10-oxo-cis-12,cis-15-octadecadienoic acid or 10-oxo-cis-6,cis-12,cis-15-octadecatrienoic acid.

[7] The method of [5] or [6], wherein the isomerase is derived from lactic acid bacteria.

[8] The method of [7], wherein the lactic acid bacteria is Lactobacillus plantarum FERM BP-10549 strain.

[9] A method of producing an oxo fatty acid having 18 carbon atoms and a carbonyl group at the 10-position, and not having a double bond at the 11- and 12-positions from an oxo fatty acid having 18 carbon atoms, a carbonyl group at the 10-position and a trans-type double bond at the 11-position by a saturase.

[10] The method of [9], wherein the oxo fatty acid having 18 carbon atoms, a carbonyl group at the 10-position and a trans-type double bond at the 11-position is 10-oxo-trans-11-octadecenoic acid, 10-oxo-cis-6,trans-11-octadecadienoic acid, 10-oxo-trans-11,cis-15-octadecadienoic acid or 10-oxo-cis-6,trans-11,cis-15-octadecatrienoic acid.

[11] The method of [9] or [10], wherein the saturase is derived from lactic acid bacteria.

[12] The method of [11], wherein the lactic acid bacteria is Lactobacillus plantarum FERM BP-10549 strain.

[13] An enzyme protein of any of the following (a)-(c):
(a) an enzyme protein consisting of the amino acid sequence shown in SEQ ID NO: 2,
(b) a protein comprising an amino acid sequence which is the amino acid sequence shown in SEQ ID NO: 2 wherein one or plural amino acids are deleted and/or substituted and/or inserted and/or added, and having an enzyme activity of catalyzing the saturation reaction in [9],
(c) a protein encoded by a base sequence that hybridizes to a nucleic acid consisting of a complementary chain sequence of the base sequence shown in SEQ ID NO: 1 under stringent conditions, and having an enzyme activity to catalyze the saturation reaction in [9].

[14] A nucleic acid encoding the enzyme protein of [13].

[15] A vector comprising the nucleic acid of [14].

[16] A host cell transformed with the vector of [15].

[17] A method of producing an enzyme, comprising culturing the host cell of [16], and recovering the enzyme protein of [13] from the culture.

[18] The method of [9], wherein the saturase is the protein of [13].

[19] A method of producing a hydroxylated fatty acid having 18 carbon atoms, a hydroxyl group at the 10-position and a trans-type double bond at the 11-position from an oxo fatty acid having 18 carbon atoms, a carbonyl group at the 10-position and a trans-type double bond at the 11-position, by a dehydrogenase reaction.

[20] The method of [19], wherein the oxo fatty acid having 18 carbon atoms, a carbonyl group at the 10-position and a trans-type double bond at the 11-position is 10-oxo-trans-11-octadecenoic acid, 10-oxo-cis-6,trans-11-octadecadienoic acid, 10-oxo-trans-11,cis-15-octadecadienoic acid or 10-oxo-cis-6,trans-11,cis-15-octadecatrienoic acid.

[21] The method of [19] or [20], wherein the dehydrogenase is derived from lactic acid bacteria.

[22] The method of [21], wherein the lactic acid bacteria is Lactobacillus plantarum FERM BP-10549 strain.

[23] A method of producing a hydroxylated fatty acid having 18 carbon atoms and a hydroxyl group at the 10-position, and not having a double bond at the 11- and 12-positions from an oxo fatty acid having 18 carbon atoms and a carbonyl group at the 10-position and not having a double bond at the 11- and 12-positions, by a dehydrogenase reaction.

[24] The method of [23], wherein the oxo fatty acid having 18 carbon atoms and a carbonyl group at the 10-position and not having a double bond at the 11- and 12-positions is 10-oxooctadecanoic acid, 10-oxo-cis-6-octadecenoic acid, 10-oxo-cis-15-octadecenoic acid or 10-oxo-cis-6,cis-15-octadecadienoic acid.

[25] The method of [23] or [24], wherein the dehydrogenase is derived from lactic acid bacteria.

[26] The method of [25], wherein the lactic acid bacteria is Lactobacillus plantarum FERM BP-10549 strain.

[27] A method of producing a conjugated fatty acid having a cis-type double bond at the 9-position and a trans-type double bond at the 11-position or a conjugated fatty acid having a trans-type double bond at the 9- and 11-positions from a hydroxylated fatty acid having 18 carbon atoms, a hydroxyl group at the 10-position and a trans-type double bond at the 11-position by a dehydratase reaction.

[28] The method of [27], wherein the hydroxylated fatty acid having 18 carbon atoms, a hydroxyl group at the 10-position and a trans-type double bond at the 11-position is 10-hydroxy-trans-11-octadecenoic acid, 10-hydroxy-cis-6,trans-11-octadecadienoic acid, 10-hydroxy-trans-11,cis-15-octadecadienoic acid or 10-hydroxy-cis-6,trans-11,cis-15-octadecatrienoic acid.

[29] The method of [27] or [28], wherein the dehydratase is derived from lactic acid bacteria.

[30] The method of [29], wherein the lactic acid bacteria is Lactobacillus plantarum FERM BP-10549 strain.

[31] A method of producing a partially saturated fatty acid having a cis-type double bond at the 9-position or a partially saturated fatty acid having a trans-type double bond at the 10-position from a hydroxylated fatty acid having 18 carbon atoms and a hydroxyl group at the 10-position, and not having a double bond at the 11- and 12-positions by a dehydratase reaction.
[32] The method of [31], wherein the hydroxylated fatty acid having 18 carbon atoms and a hydroxyl group at the 10-position, and not having a double bond at the 11- and 12-positions is 10-hydroxyoctadecanoic acid, 10-hydroxy-cis-6-octadecenoic acid, 10-hydroxy-cis-15-octadecenoic acid or 10-hydroxy-cis-6,cis-15-octadecadienoic acid.
[33] The method of [31] or [32], wherein the dehydratase is derived from lactic acid bacteria.
[34] The method of [33], wherein the lactic acid bacteria is *Lactobacillus plantarum* FERM BP-10549 strain.
[35] A method of producing a conjugated fatty acid having a cis-type double bond at the 9- and 12-positions or a conjugated fatty acid having a trans-type double bond at the 10-position and a cis-type double bond at the 12-position from a hydroxylated fatty acid having 18 carbon atoms, a hydroxyl group at the 10-position and a cis-type double bond at the 12-position by a dehydratase reaction.
[36] The method of [35], wherein the hydroxylated fatty acid having 18 carbon atoms, a hydroxyl group at the 10-position and a cis-type double bond at the 12-position is 10-hydroxy-cis-12-octadecenoic acid, 10-hydroxy-cis-6,cis-12-octadecadienoic acid, 10-hydroxy-cis-12,cis-15-octadecadienoic acid or 10-hydroxy-cis-6,cis-12,cis-15-octadecatrienoic acid.
[37] The method of [35] or [36], wherein the dehydratase is derived from lactic acid bacteria.
[38] The method of [37], wherein the lactic acid bacteria is *Lactobacillus plantarum* FERM BP-10549 strain.

Effect of the Invention

In the present invention, a conventionally-unknown saturase (CLA-ER) was found and combined with known enzymes, based on which the full particulars of the unsaturated fatty acid metabolic pathway of lactic acid bacteria was clarified. Furthermore, a multi-step enzyme reaction can produce an oxo fatty acid, a more efficient conversion can be performed by changing a part of said reaction to a chemical oxidation reaction, and oxo fatty acid can be produced in a large amount. Also, rare fatty acid can be efficiently produced from oxo fatty acid, and the oxo fatty acid, rare fatty acid and the like are extremely useful since they can be used in various fields of medicament, food, cosmetic and the like.

BRIEF DESCRIPTION OF THE DRAWINGS

The FIGURE shows the whole image of the production method of the oxo fatty acid and rare fatty acid of the present invention, wherein linoleic acid was used as a starting material.

DESCRIPTION OF EMBODIMENTS

The present invention is explained in detail below.
The present invention provides a method of producing useful rare fatty acids such as oxo fatty acid, hydroxylated fatty acid, conjugated fatty acid, partially saturated fatty acid and the like, which comprises performing each reaction of the unsaturated fatty acid metabolism pathway of lactic acid bacteria by enzyme methods (and chemically where necessary for a reaction with low enzyme reaction efficiency) in an appropriate combination. One embodiment of an overall reaction system is shown in the FIGURE.

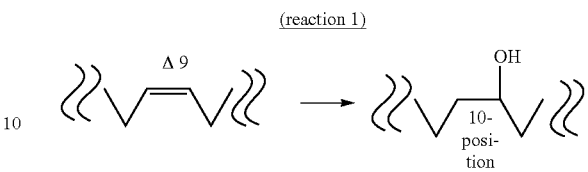

(reaction 1)

The first aspect of the present invention provides a method of producing an oxo fatty acid having 18 carbon atoms and a carbonyl group at the 10-position (hereinafter sometimes to be abbreviated as "10-oxo fatty acid") from an unsaturated fatty acid having 18 carbon atoms and a cis-type double bond at the 9-position (hereinafter sometimes to be abbreviated as "cis-9 unsaturated fatty acid") by two-step reaction. In the first reaction (reaction 1), a hydroxylated fatty acid having 18 carbon atoms and a hydroxyl group at the 10-position (hereinafter sometimes to be abbreviated as "10-hydroxyfatty acid") is produced from cis-9 unsaturated fatty acid by a hydratase reaction.

The substrate in "reaction 1" is not particularly limited as long as it is an unsaturated fatty acid having 18 carbon atoms and a cis-type double bond at the 9-position, and examples thereof include monoeneoic acid (18:1), dienoic acid (18:2), trienoic acid (18:3), tetraenoic acid (18:4), pentaenoic acid (18:5) and the like. More preferred are dienoic acid, trienoic acid and tetraenoic acid, and particularly preferred are dienoic acids and trienoic acids. In the present specification, "fatty acid" encompasses not only free acids but also ester form, salt with basic compound and the like.

Examples of the monoenoic acid include oleic acid, ricinoleic acid and the like.

Examples of the dienoic acid include linoleic acid (cis-9,cis-12-18:2), cis-9,trans-11-octadecadienoic acid (cis-9,trans-11-18:2) and the like.

Examples of the trienoic acids include α-linolenic acid (cis-9,cis-12,cis-15-18:3), γ-linolenic acid (cis-6,cis-9,cis-12-18:3) and the like.

Examples of the tetraenoic acid include stearidonic acid (cis-6,cis-9,cis-12,cis-15-18:4) and the like.

While hydratase that catalyzes reaction 1 is not particularly limited as long as it is an enzyme capable of utilizing the above-mentioned cis-9 unsaturated fatty acid as a substrate and capable of converting to 10-hydroxyfatty acid, for example, lactic acid bacteria-derived fatty acid-hydratase (CLA-HY) is preferable. More preferred is *Lactobacillus plantarum*-derived CLA-HY, and particularly preferred is *L. plantarum* FERM BP-10549 strain-derived CLA-HY. CLA-HY can be obtained by the method described in JP-A-2007-259712, or the method described in the below-mentioned Examples. Hydratase may be a purified one or a crudely purified one. Alternatively, hydratase may be expressed in fungus such as *Escherichia coli* and the like and the fungus itself may be used or culture medium thereof may be used. Furthermore, the enzyme may be of a free type, or immobilized by various carriers.

The hydratase reaction may be performed in a suitable buffer (e.g., phosphate buffer, tris buffer, borate buffer etc.) by mixing cis-9 unsaturated fatty acid, which is a substrate, and hydratase at suitable concentrations and incubating the mixture. The substrate concentration is, for example, 1-100 g/L, preferably 10-50 g/L, more preferably 20-40 g/L. The amount of hydratase to be added is, for example, 0.001-10 mg/ml, preferably 0.1-5 mg/ml, more preferably 0.2-2 mg/ml.

A "cofactor" may be used for reaction 1 and, for example, NADH, NADPH, $FADH_2$ and the like can be used. The concentration of addition may be any as long as the hydration reaction proceeds efficiently. It is preferably 0.001-20 mM, more preferably 0.01-10 mM.

Furthermore, an "activator" may be used for the enzyme reaction and, for example, one or more compounds selected from the group consisting of potassium molybdate, disodium molybdate(VI) anhydrate, disodium molybdate(VI) dihydrate, sodium orthovanadate(V), sodium metavanadate (V), potassium tungstate(VI), sodium tungstate(VI) anhydrate and sodium tungstate(VI) dihydrate can be mentioned. The concentration of addition thereof may be any as long as the hydration reaction proceeds efficiently. It is preferably 0.1-20 mM, more preferably 1-10 mM.

Reaction 1 is desirably performed within the ranges of preferable temperature and preferable pH of hydratase. For example, the reaction temperature is 5-50° C., preferably 20-45° C. The pH of the reaction mixture is pH 4-10, preferably pH 5-9. The reaction time is not particularly limited and it is, for example, 10 min-72 hr, preferably 30 min-36 hr.

In one preferable one embodiment of the present invention, hydratase is provided to the reaction system in the form of recombinant cells (e.g., *Escherichia coli, Bacillus subtilis*, yeast, insect cell, animal cell etc.) introduced with an expression vector containing a nucleic acid encoding same. In this case, the hydratase reaction can also be performed by cultivating the cells in a liquid medium suitable for the culture of the cells and added with a substrate and, where necessary, a cofactor and an activator.

(reaction 2)

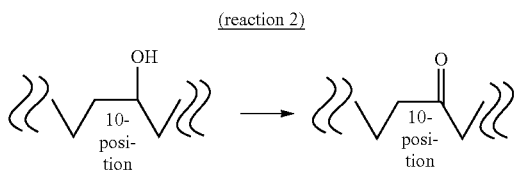

In the second reaction (reaction 2) of the first aspect of the present invention, an oxo fatty acid having 18 carbon atoms and a carbonyl group at the 10-position (hereinafter sometimes to be abbreviated as "10-oxo fatty acid") is produced from 10-hydroxyfatty acid by a dehydrogenase reaction or chemical oxidation using chromic acid.

While the dehydrogenase that catalyzes reaction 2 is not particularly limited as long as it is an enzyme capable of utilizing 10-hydroxyfatty acid as a substrate and capable of converting to 10-oxo fatty acid, for example, lactic acid bacteria-derived hydroxylated fatty acid-dehydrogenase (CLA-DH) is preferable. More preferred is *Lactobacillus plantarum*-derived CLA-DH, and particularly preferred is *L. plantarum* FERM BP-10549 strain-derived CLA-DH. CLA-DH can be obtained by the method described in JP-A-2007-259712, or the method described in the below-mentioned Examples. Dehydrogenase may be a purified one or a crudely purified one. Alternatively, dehydrogenase may be expressed in fungus such as *Escherichia coli* and the like and the fungus itself may be used or culture medium thereof may be used. Furthermore, the enzyme may be of a free type, or immobilized by various carriers.

The dehydrogenase reaction may be performed in a suitable buffer (e.g., phosphate buffer, tris buffer, borate buffer etc.) by mixing 10-hydroxyfatty acid, which is a substrate, and dehydrogenase at suitable concentrations and incubating the mixture. The substrate concentration is, for example, 1-100 g/L, preferably 10-50 g/L, more preferably 20-40 g/L. The amount of dehydrogenase to be added is, for example, 0.001-10 mg/ml, preferably 0.1-5 mg/ml, more preferably 0.2-2 mg/ml.

A "cofactor" may be used for reaction 2 and, for example, NAD, NADP, FAD and the like can be used. The concentration of addition may be any as long as the oxidation reaction proceeds efficiently. It is preferably 0.001-20 mM, more preferably 0.01-10 mM.

Furthermore, an "activator" may be used for the enzyme reaction and, for example, compounds similar to those recited as examples in the above-mentioned reaction 1 can be used at a similar addition concentration.

Reaction 2 is desirably performed within the ranges of preferable temperature and preferable pH of dehydrogenase. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one embodiment of the present invention, dehydrogenase is provided to the reaction system in the form of recombinant cells (e.g., *Escherichia coli, Bacillus subtilis*, yeast, insect cell, animal cell etc.) introduced with an expression vector containing a nucleic acid encoding same. In this case, the oxidation reaction can also be performed by cultivating the cells in a liquid medium suitable for the culture of the cells and added with a substrate and, where necessary, a cofactor and an activator.

As shown in the below-mentioned Examples 9 and 11, the present inventors have found that the conversion efficiency of 10-hydroxyfatty acid to 10-oxo fatty acid is comparatively low when *L. plantarum* FERM BP-10549 strain-derived CLA-DH is used as dehydrogenase. Therefore, they changed reaction 2 to a chemical oxidation using chromic acid, whereby extremely high conversion efficiency could be successfully obtained. Accordingly, in the first aspect of the present invention, the second reaction is more preferably performed by chemical oxidation.

As the chemical oxidation, methods known per se, for example, chromic acid oxidation, preferably Jones oxidation and the like can be mentioned. As the chromic acid, salts and complexes of the compound such as anhydrous chromic acid $CrO_3$, chromic acid $H_2CrO_4$ and dichromic acid $H_2Cr_2O_7$ can be used.

(reaction 3)

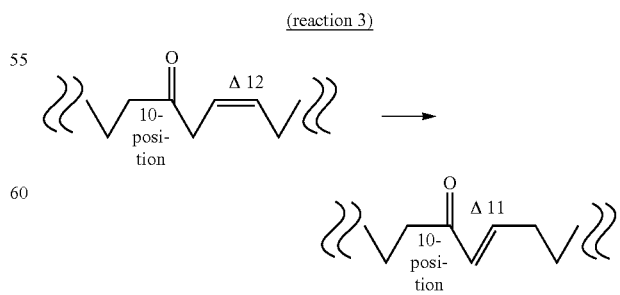

The second aspect of the present invention provides a method of producing an oxo fatty acid having 18 carbon atoms, a carbonyl group at the 10-position and a trans-type double bond at the 11-position (hereinafter sometimes to be abbreviated as "10-oxo,trans-11 fatty acid") from an oxo fatty acid having 18 carbon atoms, a carbonyl group at the 10-position and a cis-type double bond at the 12-position (hereinafter sometimes to be abbreviated as "10-oxo,cis-12 fatty acid") by an isomerase reaction (reaction 3).

The "substrate" of reaction 3 is not particularly limited as long as it is 10-oxo,cis-12 fatty acid induced from an unsaturated fatty acid having 18 carbon atoms and a cis-type double bond at the 9- and 12-positions, by the above-mentioned reactions 1 and 2. Examples thereof include 10-oxo-cis-12-octadecenoic acid (KetoA) induced from linoleic acid, 10-oxo-cis-12,cis-15-octadecadienoic acid (αKetoA) induced from α-linolenic acid, 10-oxo-cis-6,cis-12-octadecadienoic acid (γKetoA) induced from γ-linolenic acid, 10-oxo-cis-6, cis-12, cis-15-octadecatrienoic acid (sKetoA) induced from stearidonic acid and the like. It is needless to say that the substrate may be obtained by a method other than reactions 1 and 2.

While isomerase that catalyzes reaction 3 is not particularly limited as long as it is an enzyme capable of utilizing the above-mentioned 10-oxo,cis-12 fatty acid as a substrate and capable of converting to 10-oxo,trans-11 fatty acid, for example, lactic acid bacteria-derived oxo fatty acid-isomerase (CLA-DC) is preferable. More preferred is *Lactobacillus plantarum*-derived CLA-DC, and particularly preferred is *L. plantarum* FERM BP-10549 strain-derived CLA-DC. CLA-DC can be obtained by the method described in JP-A-2007-259712, or the method described in the below-mentioned Examples. Isomerase may be a purified one or a crudely purified one. Alternatively, isomerase may be expressed in fungus such as *Escherichia coli* and the like and the fungus itself may be used or culture medium thereof may be used. Furthermore, the enzyme may be of a free type, or immobilized by various carriers.

The isomerase reaction may be performed in a suitable buffer (e.g., phosphate buffer, tris buffer, borate buffer etc.) by mixing 10-oxo,cis-12 fatty acid, which is a substrate, and isomerase at suitable concentrations and incubating the mixture. The substrate concentration is, for example, 1-100 g/L, preferably 10-50 g/L, more preferably 20-40 g/L. The amount of isomerase to be added is, for example, 0.001-10 mg/ml, preferably 0.1-5 mg/ml, more preferably 0.2-2 mg/ml.

An "activator" may be used for the isomerase reaction and, for example, compounds similar to those recited as examples in the above-mentioned reaction 1 can be used at a similar addition concentration.

Reaction 3 is desirably performed within the ranges of preferable temperature and preferable pH of isomerase. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one preferable embodiment of the present invention, isomerase is provided to the reaction system in the form of recombinant cells (e.g., *Escherichia coli*, *Bacillus subtilis*, yeast, insect cell, animal cell etc.) introduced with an expression vector containing a nucleic acid encoding same. In this case, the isomerase reaction can also be performed by cultivating the cells in a liquid medium suitable for the culture of the cells and added with a substrate and, where necessary, an activator.

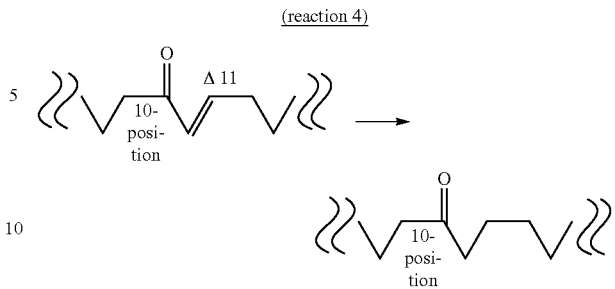

(reaction 4)

The third aspect of the present invention provides a method of producing an oxo fatty acid having 18 carbon atoms and a carbonyl group at the 10-position and not having a double bond at the 11- and 12-positions (hereinafter sometimes to be abbreviated as "10-oxo,11,12-saturated fatty acid") from an oxo fatty acid having 18 carbon atoms, a carbonyl group at the 10-position and a trans-type double bond at the 11-position (10-oxo,trans-11 fatty acid) by a saturase reaction (reaction 4).

The "substrate" of reaction 4 is not particularly limited as long as it is 10-oxo,trans-11 fatty acid produced by the above-mentioned reaction 3. Examples thereof include 10-oxo-trans-11-octadecenoic acid (KetoC) induced from 10-oxo-cis-12-octadecenoic acid (KetoA), 10-oxo-trans-11, cis-15-octadecadienoic acid (to be also referred to as "αKetoC") induced from 10-oxo-cis-12,cis-15-octadecadienoic acid (to be also referred to as "αKetoA"), 10-oxo-cis-6,trans-11-octadecadienoic acid (to be also referred to as "γKetoC") induced from 10-oxo-cis-6,cis-12-octadecadienoic acid (to be also referred to as "γKetoA"), 10-oxo-cis-6,trans-11,cis-15-octadecatrienoic acid (to be also referred to as "sKetoC") induced from 10-oxo-cis-6,cis-12,cis-15-octadecatrienoic acid (to be also referred to as "sKetoA") and the like. It is needless to say that the substrate may be obtained by a method other than reaction 3.

While saturase that catalyzes reaction 4 is not particularly limited as long as it is an enzyme capable of utilizing the above-mentioned 10-oxo,trans-11 fatty acid as a substrate and capable of converting to 10-oxo,11,12-saturated fatty acid, for example, oxo fatty acid-enone reductase (CLA-ER) derived from lactic acid bacteria isolated in the present invention is preferable. More preferred is *Lactobacillus plantarum*-derived CLA-ER, and particularly preferred is *L. plantarum* FERM BP-10549 strain-derived CLA-ER.

The novel enzyme "CLA-ER" of the present invention is
(a) an enzyme protein consisting of the amino acid sequence shown in SEQ ID NO: 2,
(b) a protein comprising an amino acid sequence which is the amino acid sequence shown in SEQ ID NO: 2 wherein one or plural amino acids are deleted and/or substituted and/or inserted and/or added, and having an enzyme activity of catalyzing the above-mentioned reaction 4, or
(c) a protein encoded by a base sequence that hybridizes to a nucleic acid consisting of a complementary chain sequence of the base sequence shown in SEQ ID NO: 1 under stringent conditions, and having an enzyme activity to catalyze the above-mentioned reaction 4.

More specific examples of the above-mentioned (b) include a protein containing (i) an amino acid sequence which is the amino acid sequence shown in SEQ ID NO: 2, wherein 1-20, preferably 1-10, more preferably 1-several (5, 4, 3 or 2) amino acids are deleted, (ii) an amino acid sequence which is the amino acid sequence shown in SEQ ID NO: 2, wherein 1-20, preferably 1-10, more preferably 1-several number (5, 4, 3 or 2) amino acids are added, (iii) an amino acid sequence which is the amino acid sequence shown in SEQ ID NO: 2, wherein 1-20, preferably 1-10, more preferably 1-several (5, 4, 3 or 2) amino acids are inserted, (iv) an amino acid sequence which is the amino acid sequence shown in SEQ ID NO: 2, wherein 1-20, preferably 1-10, more preferably 1-several (5, 4, 3 or 2) amino acids are substituted by other amino acids, or (v) an amino acid sequence obtained by combining them. When amino acids with similar properties (e.g., glycine and alanine, valine and leucine and isoleucine, serine and threonine, aspartic acid and glutamic acid, asparagine and glutamine, lysin and arginine, cysteine and methionine, phenylalanine and tyrosine etc.) are substituted with each other and the like, a greater number of substitutions and the like are possible.

When amino acids are deleted, substituted or inserted as mentioned above, the positions of deletion, substitution and insertion are not particularly limited as long as the above-mentioned enzyme activity is maintained.

In the above-mentioned (c), the "stringent conditions" are conditions under which nucleotide sequences having high identity, for example, identity of 70, 80, 90, 95 or 99% or above, hybridize to each other and nucleotide sequences having identity lower than that do not hybridize; specifically, conditions of washing once, more preferably 2-3 times, at the salt concentration and temperature corresponding to those in the washing conditions of general Southern hybridization (60° C., 1×SSC, 0.1% SDS, preferably, 0.1×SSC, 0.1% SDS, more preferably, 68° C., 0.1×SSC, 0.1% SDS) and the like.

CLA-ER can be isolated from, for example, the fungus and culture medium of *L. plantarum* FERM BP-10549 strain by a protein separation and purification technique known per se. Alternatively, CLA-ER can also be produced as a recombinant protein by isolating a gene encoding CLA-ER according to the method described in Example 2, subcloning same into a suitable vector, introducing same into a suitable host such as *Escherichia coli* and the like and culturing same. CLA-ER may be a purified one or a crudely purified one. Alternatively, hydratase may be expressed in fungus such as *Escherichia coli* and the like and the fungus itself may be used or culture medium thereof may be used. Furthermore, the enzyme may be of a free type, or immobilized by various carriers.

As a vector containing a nucleic acid encoding CLA-ER of the present invention, one suitable for a host cell to be introduced with the vector may be appropriately selected according to the object (e.g., protein expression) and can be used. In the case of an expression vector, it contains the nucleic acid of the present invention, which is operably linked to an appropriate promoter, and preferably contains a transcription termination signal, i.e., terminator region, at the downstream of the nucleic acid of the present invention. Furthermore, it can also contain a selection marker gene for selection of a transformant (drug resistance gene, gene that complements auxotrophic mutation etc.). Also, it may contain a sequence encoding a tag sequence useful for separation and purification of the expressed protein and the like. In addition, the vector may be incorporated into the genome of a target host cell. The vector of the present invention can be introduced into a target host cell by a transformation method known per se such as a competent cell method, a protoplast method, a calcium phosphate coprecipitation method and the like.

In the present invention, the "host cell" may be any cell as long as it can express a vector containing a nucleic acid encoding CLA-ER of the present invention, and bacterium, yeast, fungi, higher eukaryotic cell and the like can be mentioned. Examples of the bacterium include gram-positive bacteria such as bacillus, Streptomyces and the like and gram negative bacteria such as *Escherichia coli* and the like. A recombinant cell introduced with a vector containing a nucleic acid encoding CLA-ER can be cultivated by a method known per se which is suitable for the host cell.

In the present invention, "purification" of CLA-ER can be performed by a method known per se, for example, fungi collected by centrifugation and the like are ruptured by ultrasonication or glass beads and the like, solid such as cell debris is removed by centrifugation and the like, and the like to give a crude enzyme solution, which is subjected to a salting out method using ammonium sulfate, sodium sulfate and the like, chromatographys such as ion exchange chromatography, gel filtration chromatography, affinity chromatography and the like, gel electrophoresis and the like.

The isomerase reaction may be performed in a suitable buffer (e.g., phosphate buffer, tris buffer, borate buffer etc.) by mixing 10-oxo,trans-11 fatty acid, which is a substrate, and saturase at suitable concentrations and incubating the mixture. The substrate concentration is, for example, 1-100 g/L, preferably 10-50 g/L, more preferably 20-40 g/L. The amount of saturase to be added is, for example, 0.001-10 mg/ml, preferably 0.1-5 mg/ml, more preferably 0.2-2 mg/ml.

A "cofactor" may be used for reaction 4 and, for example, NADH and the like can be used. The concentration of addition may be any as long as the oxidation reaction proceeds efficiently. It is preferably 0.001-20 mM, more preferably 0.01-10 mM.

Furthermore, an "activator" may be used for the enzyme reaction and, for example, compounds similar to those recited as examples in the above-mentioned reaction 1 can be used at a similar addition concentration.

Reaction 4 is desirably performed within the ranges of preferable temperature and preferable pH of saturase. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one preferable embodiment of the present invention, saturase is provided to the reaction system in the form of recombinant cells (e.g., *Escherichia coli*, *Bacillus subtilis*, yeast, insect cell, animal cell etc.) introduced with an expression vector containing a nucleic acid encoding same. In this case, the saturase reaction can also be performed by cultivating the cells in a liquid medium suitable for the culture of the cells and added with a substrate and, where necessary, an activator.

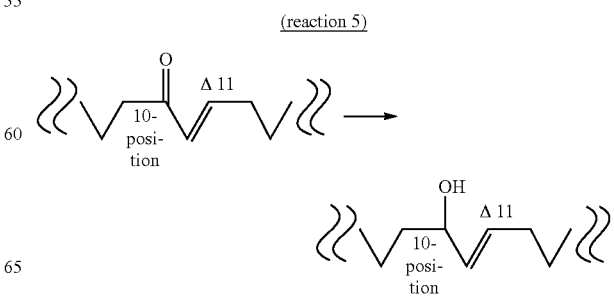

(reaction 5)

-continued (reaction 6)

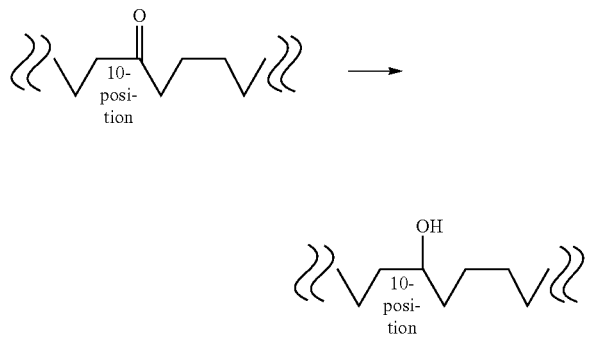

The fourth aspect of the present invention provides a method of producing a hydroxylated fatty acid having 18 carbon atoms, a hydroxyl group at the 10-position and a trans-type double bond at the 11-position (hereinafter sometimes to be abbreviated as "10-hydroxy,trans-11 fatty acid") from an oxo fatty acid having 18 carbon atoms, a carbonyl group at the 10-position and a trans-type double bond at the 11-position (10-oxo,trans-11 fatty acid) by a dehydrogenase reaction (reaction 5) or a method of producing a hydroxylated fatty acid having 18 carbon atoms and a hydroxyl group at the 10-position, and not having a double bond at the 11- and 12-positions (hereinafter sometimes to be abbreviated as "10-hydroxy,11,12-saturated fatty acid") from an oxo fatty acid having 18 carbon atoms and a carbonyl group at the 10-position and not having a double bond at the 11- and 12-positions (10-oxo,11,12-saturated fatty acid) by a dehydrogenase reaction (reaction 6).

The "substrate" of reaction 5 is not particularly limited as long as it is 10-oxo,trans-11 fatty acid produced by the above-mentioned reaction 3. Examples thereof include 10-oxo-trans-11-octadecenoic acid (KetoC) induced from 10-oxo-cis-12-octadecenoic acid (KetoA), 10-oxo-trans-11, cis-15-octadecadienoic acid (to be also referred to as "αKetoC") induced from 10-oxo-cis-12,cis-15-octadecadienoic acid (to be also referred to as "αKetoA"), 10-oxo-cis-6,trans-11-octadecadienoic acid (to be also referred to as "γKetoC") induced from 10-oxo-cis-6,cis-12-octadecadienoic acid (to be also referred to as "γKetoA"), 10-oxo-cis-6,trans-11,cis-15-octadecatrienoic acid (to be also referred to as "sKetoC") induced from 10-oxo-cis-6,cis-12,cis-15-octadecatrienoic acid (to be also referred to as "sKetoA") and the like. It is needless to say that the substrate may be obtained by a method other than reaction 3.

On the other hand, the "substrate" of reaction 6 is not particularly limited as long as it is 10-oxo,11,12-saturated fatty acid produced by the above-mentioned reaction 4. Examples thereof include 10-oxooctadecanoic acid (KetoB) induced from 10-oxo-trans-11-octadecenoic acid (KetoC), 10-oxo-cis-15-octadecenoic acid (to be also referred to as "αKetoB") induced from 10-oxo-trans-11,cis-15-octadecadienoic acid (αKetoC), 10-oxo-cis-6-octadecenoic acid (to be also referred to as "γKetoB") induced from 10-oxo-cis-6,trans-11-octadecadienoic acid (γKetoC), 10-oxo-cis-6,cis-15-octadecadienoic acid (to be also referred to as "sKetoB") induced from 10-oxo-cis-6,trans-11,cis-15-octadecatrienoic acid (sKetoC) and the like. It is needless to say that the substrate may be obtained by a method other than reaction 4.

While the dehydrogenase that catalyzes reaction 5 or reaction 6 is not particularly limited as long as it is an enzyme capable of utilizing 10-oxo,trans-11 fatty acid or 10-oxo,11,12-saturated fatty acid as a substrate and capable of converting to 10-hydroxy,trans-11 fatty acid or 10-hydroxy,11,12-saturated fatty acid, for example, lactic acid bacteria-derived hydroxylated fatty acid-dehydrogenase (CLA-DH) is preferable. More preferred is Lactobacillus plantarum-derived CLA-DH, and particularly preferred is L. plantarum FERM BP-10549 strain-derived CLA-DH. While CLA-DH catalyzes the oxidation reaction in the above-mentioned reaction 2, it can also catalyze the reduction reaction in reaction 5 or reaction 6 as a reverse reaction.

Dehydrogenase may be a purified one or a crudely purified one. Alternatively, dehydrogenase may be expressed in fungus such as Escherichia coli and the like and the fungus itself may be used or culture medium thereof may be used. Furthermore, the enzyme may be of a free type, or immobilized by various carriers.

The reduction reaction by dehydrogenase may be performed in a suitable buffer (e.g., phosphate buffer, tris buffer, borate buffer etc.) by mixing 10-oxo,trans-11 fatty acid or 10-oxo,11,12-saturated fatty acid, which is a substrate, and dehydrogenase at suitable concentrations and incubating the mixture. The substrate concentration is, for example, 1-100 g/L, preferably 10-50 g/L, more preferably 20-40 g/L. The amount of dehydrogenase to be added is, for example, 0.001-10 mg/ml, preferably 0.1-5 mg/ml, more preferably 0.2-2 mg/ml.

A "cofactor" may be used for reaction 5 and reaction 6 and, for example, NADH, NADPH, $FADH_2$ and the like can be used. The concentration of addition may be any as long as the reduction reaction proceeds efficiently. It is preferably 0.001-20 mM, more preferably 0.01-10 mM.

Furthermore, an "activator" may be used for the enzyme reaction and, for example, compounds similar to those recited as examples in the above-mentioned reaction 1 can be used at a similar addition concentration.

Reaction 5 and reaction 6 are desirably performed within the ranges of preferable temperature and preferable pH of dehydrogenase. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one preferable one embodiment of the present invention, dehydrogenase is provided to the reaction system in the form of recombinant cells (e.g., Escherichia coli, Bacillus subtilis, yeast, insect cell, animal cell etc.) introduced with an expression vector containing a nucleic acid encoding same. In this case, the reduction reaction can also be performed by cultivating the cells in a liquid medium suitable for the culture of the cells and added with a substrate and, where necessary, a cofactor and an activator.

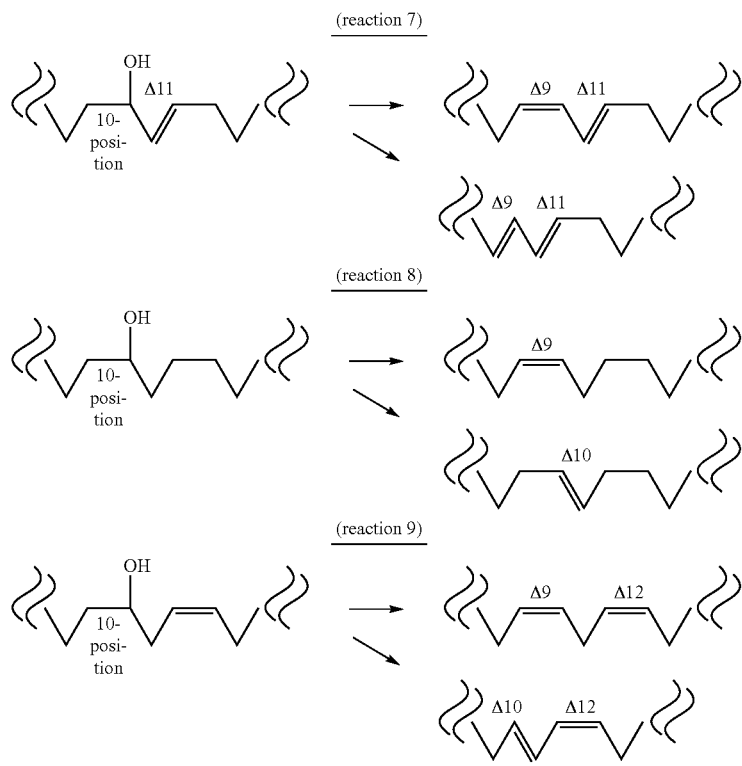

(reaction 7)

(reaction 8)

(reaction 9)

The fifth aspect of the present invention provides a method of producing a conjugated fatty acid having a cis-type double bond at the 9-position and a trans-type double bond at the 11-position (hereinafter sometimes to be abbreviated as "cis-9,trans-11 conjugated fatty acid") or a conjugated fatty acid having a trans-type double bond at the 9- and 11-positions (hereinafter sometimes to be abbreviated as "trans-9,trans-11 conjugated fatty acid") from a hydroxylated fatty acid having 18 carbon atoms, a hydroxyl group at the 10-position and a trans-type double bond at the 11-position (10-hydroxy,trans-11 fatty acid) by a dehydratase reaction (reaction 7), a method of producing a partially saturated fatty acid having a cis-type double bond at the 9-position (hereinafter sometimes to be abbreviated as "cis-9 partially saturated fatty acid") or a partially saturated fatty acid having a trans-type double bond at the 10-position (hereinafter sometimes to be abbreviated as "trans-10 partially saturated fatty acid") from a hydroxylated fatty acid having 18 carbon atoms and a hydroxyl group at the 10-position, and not having a double bond at the 11- and 12-positions (10-hydroxy,11,12-saturated fatty acid) by a dehydratase reaction (reaction 8), or a method of producing a unsaturated fatty acid having a cis-type double bond at the 9- and 12-positions (hereinafter sometimes to be abbreviated as "cis-9,cis-12 unsaturated fatty acid") or a conjugated fatty acid having a trans-type double bond at the 10-position and a cis-type double bond at the 12-position (hereinafter sometimes to be abbreviated as "trans-10,cis-12 conjugated fatty acid") from a hydroxylated fatty acid having 18 carbon atoms, a hydroxyl group at the 10-position and a cis-type double bond at the 12-position (hereinafter sometimes to be abbreviated as "10-hydroxy,cis-12 fatty acid") by a dehydratase reaction (reaction 9).

The "substrate" of reaction 7 is not particularly limited as long as it is 10-hydroxy,trans-11 fatty acid produced by the above-mentioned reaction 5. Examples thereof include 10-hydroxy-trans-11-octadecenoic acid (HYC) induced from 10-oxo-trans-11-octadecenoic acid (KetoC), 10-hydroxy-trans-11,cis-15-octadecadienoic acid (to be also referred to as "αHYC") induced from 10-oxo-trans-11,cis-15-octadecadienoic acid (αKetoC), 10-hydroxy-cis-6,trans-11-octadecadienoic acid (to be also referred to as "γHYC") induced from 10-oxo-cis-6,trans-11-octadecadienoic acid (γKetoC), 10-hydroxy-cis-6,trans-11,cis-15-octadecatrienoic acid (to be also referred to as "sHYC") induced from 10-oxo-cis-6,trans-11,cis-15-octadecatrienoic acid (sKetoC) and the like. It is needless to say that the substrate may be obtained by a method other than reaction 5.

The "substrate" of reaction 8 is not particularly limited as long as it is 10-hydroxy,11,12-saturated fatty acid produced by the above-mentioned reaction 6. Examples thereof include 10-hydroxyoctadecanoic acid (HYB) induced from 10-oxooctadecanoic acid (KetoB), 10-hydroxy-cis-15-octadecenoic acid (to be also referred to as "αHYB") induced from 10-oxo-cis-15-octadecenoic acid (αKetoB), 10-hydroxy-cis-6-octadecenoic acid (to be also referred to as "γHYB") induced from 10-oxo-cis-6-octadecenoic acid (γKetoB), 10-hydroxy-cis-6,cis-15-octadecadienoic acid (to be also referred to as "sHYB") induced from 10-oxo-cis-6,cis-15-octadecadienoic acid (sKetoB) and the like. It is needless to say that the substrate may be obtained by a method other than reaction 6.

The "substrate" of reaction 9 is not particularly limited as long as it is 10-hydroxy,cis-12 fatty acid that can be produced from an unsaturated fatty acid having a cis-type double bond at the 9- and 12-positions by the above-mentioned reaction 1. Examples thereof include 10-hydroxy-cis-12-octadecenoic acid (HYA) induced from linoleic acid, 10-hydroxy-cis-12,cis-15-octadecadienoic acid (to be also referred to as "αHYA") induced from α-linolenic acid, 10-hydroxy-cis-6,cis-12-octadecadienoic acid (to be also referred to as "γHYA") induced from γ-linolenic acid, 10-hydroxy-cis-6,cis-12,cis-15-octadecatrienoic acid (to be also referred to as "sHYA") induced from stearidonic acid and the like. It is needless to say that the substrate may be obtained by a method other than reaction 1.

While hydratase that catalyzes reactions 7-9 is not particularly limited as long as it is an enzyme capable of utilizing the above-mentioned 10-hydroxy,trans-11 fatty acid, 10-hydroxy,11,12-saturated fatty acid or 10-hydroxy, cis-12 fatty acid as a substrate and capable of converting to cis-9,trans-11 conjugated fatty acid or trans-9,trans-11 conjugated fatty acid, cis-9 partially saturated fatty acid or trans-10 partially saturated fatty acid, or cis-9,cis-12 unsaturated fatty acid or trans-10,cis-12 conjugated fatty acid, for example, lactic acid bacteria-derived fatty acid-hydratase (CLA-HY) is preferable. More preferred is *Lactobacillus plantarum*-derived CLA-HY, and particularly preferred is *L. plantarum* FERM BP-10549 strain-derived CLA-HY. While CLA-HY catalyzes the hydration reaction in the above-mentioned reaction 1, it can also catalyze the dehydration reaction in reactions 7-9 as a reverse reaction.

Dehydratase may be a purified one or a crudely purified one. Alternatively, hydratase may be expressed in fungus such as *Escherichia coli* and the like and the fungus itself may be used or culture medium thereof may be used. Furthermore, the enzyme may be of a free type, or immobilized by various carriers.

The dehydratase reaction may be performed in a suitable buffer (e.g., phosphate buffer, tris buffer, borate buffer etc.) by mixing 10-hydroxy,trans-11 fatty acid, 10-hydroxy,trans-11,12-saturated fatty acid or 10-hydroxy,cis-12 fatty acid, which is a substrate, and dehydratase at suitable concentrations and incubating the mixture. The substrate concentration is, for example, 1-100 g/L, preferably 10-50 g/L, more preferably 20-40 g/L. The amount of dehydratase to be added is, for example, 0.001-10 mg/ml, preferably 0.1-5 mg/ml, more preferably 0.2-2 mg/ml.

A "cofactor" may be used for reactions 7-9 and, for example, NADH, NADPH, $FADH_2$ and the like can be used. The concentration of addition may be any as long as the dehydration reaction proceeds efficiently. It is preferably 0.001-20 mM, more preferably 0.01-10 mM.

Furthermore, an "activator" may be used for the enzyme reaction and, for example, compounds similar to those recited as examples in the above-mentioned reaction 1 can be used at a similar addition concentration.

Reactions 7-9 are desirably performed within the ranges of preferable temperature and preferable pH of dehydratase. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one preferable embodiment of the present invention, dehydratase is provided to the reaction system in the form of recombinant cells (e.g., *Escherichia coli, Bacillus subtilis,* yeast, insect cell, animal cell etc.) introduced with an expression vector containing a nucleic acid encoding same. In this case, the dehydration reaction can also be performed by cultivating the cells in a liquid medium suitable for the culture of the cells and added with a substrate and, where necessary, a cofactor and an activator.

The oxo fatty acid, hydroxylated fatty acid, conjugated fatty acid or partially saturated fatty acid (hereinafter to be comprehensively referred to as "oxo fatty acid and the like") obtained in the present invention can be used by being blended with, for example, medicament, food or cosmetic agent based on the conventionally-known physiological activity.

Examples of the dosage form of a medicament containing oxo fatty acid and the like include powder, granule, pill, soft capsule, hard capsules, tablet, chewable tablet, quick-integrating tablet, syrup, liquid, suspension, suppository, ointment, cream, gel, adhesive, inhalant, injection and the like. A preparation thereof is prepared according to a conventional method. Since oxo fatty acid and the like are poorly soluble in water, they are dissolved in a non-hydrophilic organic solvent such as plant-derived oil, animal-derived oil and the like or dispersed or emulsified in an aqueous solution together with an emulsifier, a dispersing agent, a surfactant and the like by a homogenizer (high-pressure homogenizer) and used.

Examples of the additives that can be used for formulating include animal and plant oils such as soybean oil, safflower oil, olive oil, germ oil, sunflower oil, beef fat, sardine oil and the like, polyvalent alcohols such as polyethylene glycol, propylene glycol, glycerol, sorbitol and the like, surfactants such as sorbitan ester of fatty acid, sucrose fatty acid ester, glycerin fatty acid ester, polyglycerin fatty acid ester and the like, excipients such as purified water, lactose, starch, crystalline cellulose, D-mannitol, lecithin, gum arabic, sorbitol solution, carbohydrate solution and the like, sweetener, colorant, pH adjuster, flavor and the like. A liquid preparation may be dissolved or suspended in water or other suitable medium when in use. Also, tablet and granules may be coated by a well-known method.

For administration in the form of an injection, intravenous, intraperitoneal, intramuscular, subcutaneous, transdermal, intraarticular, intrasynovial, intrathecal, intraperiosteum, sublingual, oral administrations and the like are preferable, and intravenous administration or intraperitoneal administration is particularly preferable. The intravenous administration may be any of drip administration and bolus administration.

Examples of the form of the "food" containing oxo fatty acid and the like obtained by the present invention include supplements (powder, granule, soft capsule, hard capsule, tablet, chewable tablet, quick-integrating tablet, syrup, liquid etc.), drinks (tea, carbonic acid drink, lactic acid drink, sport drink etc.), confectionery (gummy, jelly, gum, chocolate, cookie, candy etc.), oil, fat and oil food (mayonnaise, dressing, butter, cream, margarine etc.) and the like.

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, *Agaricus* and the like.

Examples of the "cosmetic agent" containing oxo fatty acid and the like obtained by the present invention include cream, skin milk, toner, microemulsion essence, bath powder and the like, which may be mixed with a flavor and the like.

The present invention is explained in more detail in the following by referring to Examples. The Examples are mere exemplifications of the present invention and do not limit the scope of the present invention in any manner.

EXAMPLE 1

Culture Method of *Lactobacillus plantarum* FERM BP-10549

*Lactobacillus plantarum* FERM BP-10549 in MRS stab containing 2% agar and preserved at 4° C. was inoculated in 15 ml of MRS liquid medium (manufactured by Difco; pH 6.5), and precultured at 28° C., 120 rpm for 20 hr. The main culture was performed by culturing the total amount of the preculture, inoculated to 550 ml of MRS liquid medium containing 7.7 ml of linoleic acid solution shown below, at 28° C., 120 rpm for 24 hr. The linoleic acid solution was obtained by adding 10 mg of bovine serum albumin to 50 mg of linoleic acid, suspending same in 1 ml of 0.1 M potassium phosphate buffer (pH 6.5), homogenizing the suspension by ultrasonication for 10 min, and eliminating bacteria by using a 0.45 µm filter. After culture, centrifugation at 3,000 rpm, 4° C. for 10 min gave the fungus of *Lactobacillus plantarum* FERM BP-10549.

*Lactobacillus plantarum* FERM BP-10549 strain has been deposited since Mar. 7, 2006 at incorporated administrative agency, International Patent Organism Depositary of National Institute of Advanced Industrial Science and Technology (IPOD, AIST) (now incorporated administrative agency, International Patent Organism Depositary of National Institute of Technology and Evaluation (IPOD, NITS)); Central 6, 1-1-1 Higashi, Tsukuba, Ibaraki 305-8566 Japan.

EXAMPLE 2

Cloning of Gene of Enzyme Having Amino Acid Sequence Shown in SEQ ID NO: 2 (CLA-ER:Oxo Fatty Acid-Enone Reductase)

(1) Obtainment of Genome DNA

Wet fungus (14 g) of *Lactobacillus plantarum* FERM BP-10549 was suspended in 180 ml of TEN buffer (10 mM Tris-HCl (pH 7.5); 1 mM EDTA; 10 mM NaCl). Thereto were added 9 ml of SET buffer (20% Sucrose; 50 mM EDTA; 50 mM Tris-HCl (pH 7.5)) and 135 mg of lysozyme and the mixture was incubated at 37° C. for 10 min. Then, 90 ml of TEN buffer, 9 ml of 25% SDS, 18 ml of 5 M NaCl, 180 ml of phenol, and 32 ml of chloroform were added and the mixture was gently and completely mixed. Thereafter, the mixture was centrifuged at 3,500×g for 20 min at room temperature, and the upper layer was recovered. Then, chloroform in an equal amount to the upper layer was added, the mixture was completely mixed and centrifuged at 3,500×g for 20 min at room temperature, and the upper layer was recovered. An equal amount of ethanol was added, the mixture was completely mixed and centrifuged at 3,500×g for 20 min at room temperature. The obtained precipitate was dried for 20 min in a vacuum desiccator, and dissolved in a small amount of TE buffer (10 mM Tris-HCl (pH 8.0); 1 mM EDTA). Thereto was added 20 µl of RNaseA solution, the mixture was incubated at 37° C. for 15 hr, 1.2 ml of chloroform was added, the mixture was centrifuged at 3,500×g for 20 min at room temperature and the upper layer was recovered. Thereto was added 6 ml of chloroform, the mixture was incubated at 3,500×g for 20 min at room temperature, and the upper layer was recovered. Furthermore, 6 ml of isopropanol was added, the mixture was completely mixed, incubated for 30 min at room temperature and centrifuged at 3,500×g for 20 min at room temperature. The obtained precipitate was washed with 70% ethanol, dried in a vacuum desiccator, and dissolved in TE buffer to give genome DNA.

(2) Obtainment of CLA-ER Gene by PCR

In the published full-length genome gene sequence of *Lactobacillus plantarum* WCFS1 strain, an open-reading-frame (ORF) present immediately at the downstream of CLA-DC was used as a target. A sense primer (SEQ ID NO: 3) was designed based on the sequence at 9-28 bases upstream of the 5' side of the initiation codon of ORF, and an antisense primer (SEQ ID NO: 4) was designed based on the sequence 13-31 bases downstream of the 3' side of the stop codon. Using these primers, and the genome DNA of *Lactobacillus plantarum* FERM BP-10549 as a template, PCR was performed. The base sequence of about 0.7 kbp gene segment amplified as a result of PCR was decoded. As a result, it was clarified that the gene segment contains one 654 bp ORF (SEQ ID NO: 1), which starts from the initiation codon ATG and ends at the stop codon TAA, and this gene was termed as CLA-ER gene. The CLA-ER gene encodes a protein consisting of 217 residual amino acids shown in SEQ ID NO: 2.

EXAMPLE 3

Expression of (CLA-ER) in *Escherichia coli*

A host vector system consisting of *Escherichia coli* expression vector pET101/D-TOPO (Invitrogen) and Rosetta 2 (DE3) strain was used. CACC was added to the upstream of the initiation codon ATG of CLA-ER gene of *Lactobacillus plantarum* FERM BP-10549, and PCR was performed using a sense primer (SEQ ID NO: 5) designed based on the initiation codon and the sequence of 23 bases on the 3' terminal side containing same, and an antisense primer (SEQ ID NO: 6) designed based on the sequence of 26 bases on the 5' terminal side from which the stop codon TAA had been deleted, and the genome DNA of *Lactobacillus plantarum* FERM BP-10549 as a template. An about 0.6 kbp gene segment amplified as a result of PCR was inserted into pET101/D-TOPO to construct an expression vector (pCLA-ER). Rosetta 2 (DE3) strain was transformed with pCLA-ER to give transformed Rosetta/pCLA-ER strain. The obtained Rosetta/pCLA-ER strain was aerobically cultured in 10 ml LB medium (medium containing 1% Bacto Tripton (Difco), 0.5% yeast extract, 1% sodium chloride (pH 7.0)) containing 1 mg ampicillin at 37° C., 300 rpm for 15 hr to give a preculture. The preculture (10 ml) was inoculated to 750 ml LB medium containing 75 mg ampicillin, aerobically cultured at 37° C., 100 rpm for 2 hr. Then, 1 M IPTG (750 µl) was added, and the mixture was aerobically further cultured at 20° C., 100 rpm for 15 hr. After culture, the mixture was centrifuged at 3,000 rpm for 10 min to give wet fungus of Rosetta/pCLA-ER strain. As saturase, CLA-ER expressing transformed *Escherichia coli* was used.

EXAMPLE 4

Preparation Method of Each Transformed *Escherichia coli*

Based on the report of Kishino et al. (Biochemical and Biophysical Research Communications 416 (2011) 188-193), transformed *Escherichia coli* expressing each of CLA-HY, CLA-DH, CLA-DC was prepared. As hydratase and dehydratase, CLA-HY expression transformed *Escherichia coli* was used, CLA-DC expressing transformed *Escherichia coli* was used as isomerase and CLA-DH expressing transformed *Escherichia coli* was used as dehydrogenase.

EXAMPLE 5

Purification of Dehydratase from Dehydratase Transformed *Escherichia coli*

The fungus obtained by culture was suspended in 3 ml of buffer C (40 mM imidazole, 50 mM potassium phosphate buffer (pH 8.0), 0.5 M NaCl), and the fungus was disrupted by ultrasonication. After disruption, the fungus was ultracentrifuged at 10,000×g, 4° C., for 60 min and the upper layer was recovered and purified by FPLC using affinity column (HisTrap HP) and dialysis (dialysis solution was 50 mM potassium phosphate buffer (pH 6.5)).

EXAMPLE 6

Purification of Dehydrogenase from Dehydrogenase Transformed *Escherichia coli*

The fungus obtained by culture was suspended in 3 ml of BugBuster Master Mix (Novagen), and the fungus was incubated at room temperature for 20 min. After incubation, the fungus was ultracentrifuged at 10,000×g, 4° C., for 60 min and the upper layer was recovered and purified by FPLC using gel filtration column (Superdex 200 Hiload 26/60), ion exchange column (MonoQ 10/100), gel filtration column (Superdex 200 10/300) and dialysis (dialysis solution was buffer C).

EXAMPLE 7

Production of HYA from Linoleic Acid by Using Hydratase Expressed in *Escherichia coli*

Using hydratase-induced transformed *Escherichia coli*, a production test of HYA from linoleic acid was performed. The reaction mixture was 100 mM potassium phosphate buffer (pH 6.5) containing hydratase-induced transformed *Escherichia coli* (wet fungus weight 3 g), NADH (600 mg), FAD (15 mg), linoleic acid (5 g) and BSA (1 g) and the total amount thereof was 160 ml. The reaction was performed by anaerobically shaking at 37° C., 120 rpm for 36 hr in the presence of an oxygen adsorbent Anaeropack (Mitsubishi Chemical Corporation). After the reaction, 5N HCl (1.6 ml), chloroform (200 ml) and methanol (200 ml) were added to the reaction mixture (160 ml), the mixture was stirred with a stirrer, and the chloroform layer was recovered. Furthermore, chloroform (150 ml) was added to the residual solution, the mixture was stirred well, and the chloroform layer was recovered again. The recovered chloroform layers were collectively concentrated in a rotary evaporator, and the reaction product and an unreacted substrate were extracted. A part of the extract was methylesterified, and the purity of HYA was evaluated by gas chromatography. As a result, about 80% of the extract was confirmed to be HYA.

EXAMPLE 8

Purification of HYA from Extract (Mixture Containing HYA) Obtained in Example 7

Silica gel (Wakogel® C-100) in a 10-fold weight that of the extract (mixture containing HYA) obtained in Example 7 was swollen with hexane and filled in a glass column, and sodium sulfate (anhydrous) was layered thereon. The extract (mixture containing HYA) obtained in Example 7 was suspended in an eluent of hexane:diethyl ether=8:2 and applied to the column. The eluate was flown at a flow rate of about 2 ml, and the solution discharged from the column was recovered by dividing into fractions. Each recovered fraction was analyzed by LC/MS and gas chromatography, unreacted substrate and fungus-derived lipid were removed, the eluent was changed to hexane:diethyl ether=6:4, and the fraction was further eluted. Each recovered fraction was analyzed by LC/MS and gas chromatography, and the fractions containing HYA only were collected and concentrated in a rotary evaporator. A part of the obtained final product was methylesterified, and the purity of HYA was evaluated by gas chromatography. As a result, HYA having a purity of not less than 98% was obtained.

EXAMPLE 9

Production of KetoA from HYA by Using CLA-DH Expressed in *Escherichia coli*

Using the purified dehydrogenase obtained in Example 6, a production test of KetoA from HYA was performed. The reaction mixture was 20 mM potassium phosphate buffer (pH 8.0) containing purified dehydrogenase (enzyme amount 83 µg), 0.5 mM NAD$^+$, 0.01 mM FAD and 0.1% HYA and the total amount thereof was 1 ml. The reaction was performed by anaerobically shaking at 37° C., 120 rpm for 4 hr in the presence of an oxygen adsorbent Anaeropack (Mitsubishi Chemical Corporation). After the reaction, lipid was extracted by Bligh-Dyer method from the reaction mixture and methylesterified, and the production of KetoA was evaluated by gas chromatography. As a result, production of KetoA (0.06 mg) from HYA was confirmed.

EXAMPLE 10

Production of KetoA from HYA by Using Anhydrous Chromic Acid ($CrO_3$)

To anhydrous chromic acid (2.67 g) were added sulfuric acid (2.3 ml) and water (7.7 ml), and acetone (90 ml) was added thereto to give a chromic acid solution. 2 g of HYA and 40 ml of acetone were added into an Erlenmeyer flask, and the above-mentioned chromic acid solution was added drop by drop on ice while stirring the mixture with a stirrer. When the solution turned from blue to the color of powdered green tea, the dropwise addition of the chromic acid solution was stopped and the reaction was quenched with isopropyl alcohol. The precipitated sediment was filtered with a filter paper and placed in a partitioning funnel. Diethyl ether (150 ml) and Milli Q water (300 ml) were further added and the mixture was shaken well. The diethyl ether layer was washed several times with Milli Q water. To the diethyl ether layer after washing was added an appropriate amount of sodium sulfate (anhydrous), the mixture was stirred, and the residual water was removed. The anhydrous sodium sulfate added was filtered off with a filter paper, the obtained diethyl ether layer was concentrated in a rotary evaporator, and the reaction product and an unreacted substrate were extracted. Using a part of the extract, the purity of KetoA was evaluated by LC/MS. As a result, about 95% of the extract was confirmed to be KetoA.

EXAMPLE 11

Comparison of KetoA Production Using Anhydrous Chromic Acid and KetoA Production Using CLA-DH Expressed in *Escherichia coli*

The conversion efficiency of the KetoA production method using purified dehydrogenase was 6% since 0.06 mg of KetoA was produced from 1 ml of reaction system containing 1 mg of HYA.

In contrast, the conversion efficiency of the KetoA production method using anhydrous chromic acid was about 95% since about 95% of the total fatty acid extracted from 2 g of HYA was KetoA, and drastic improvement of KetoA production efficiency was successfully achieved.

EXAMPLE 12

Purification of KetoA from Extract (Mixture Containing KetoA) Obtained in Example 10

Silica gel (Wakogel® C-100) in a 20- to 30-fold weight that of the extract (mixture containing KetoA) obtained in Example 10 was swollen with hexane and filled in a glass column, and sodium sulfate (anhydrous) was layered thereon. The extract (mixture containing KetoA) obtained in Example 10 was suspended in an eluent of hexane:diethyl ether=8:2 and applied to the column. The eluent was flown at a flow rate of about 2 ml, and the solution discharged from the column was recovered in divided fractions. Each recovered fraction was analyzed by LC/MS and gas chromatography, and the fractions containing KetoA only were collected and concentrated in a rotary evaporator. A part of the obtained final product was methylesterified, and the purity of KetoA was evaluated by gas chromatography. As a result, KetoA having a purity of not less than 98% was obtained.

EXAMPLE 13

Production of αHYA from α-Linolenic Acid by Using Hydratase Expressed in *Escherichia coli*

Using hydratase-induced transformed *Escherichia coli*, a production test of αHYA from α-linolenic acid was performed. The reaction mixture was 100 mM potassium phosphate buffer (pH 6.5) containing hydratase-induced transformed *Escherichia coli* (wet fungus weight 0.7 g), NADH (33 mg), FAD (0.8 mg), α-linolenic acid (1 g) and BSA (0.2 g) and the total amount thereof was 10 ml. The reaction was performed by anaerobically shaking at 37° C., 225 rpm for 63 hr in the presence of an oxygen adsorbent Anaeropack (Mitsubishi Chemical Corporation). After the reaction, chloroform (10 ml) and methanol (10 ml) were added, the mixture was stirred, and the chloroform layer was recovered. Furthermore, chloroform (10 ml) was added to the residual solution, the mixture was stirred well, and the chloroform layer was recovered again. The recovered chloroform layers were collectively concentrated in a rotary evaporator, and the reaction product and an unreacted substrate were extracted. A part of the extract was methylesterified, and the purity of αHYA was evaluated by gas chromatography. As a result, about 35% of the extract was confirmed to be αHYA.

EXAMPLE 14

Purification of αHYA from Extract (Mixture Containing αHYA) Obtained in Example 13

Silica gel (Wakogel® C-100) in a 20- to 30-fold weight that of the extract (mixture containing αHYA) obtained in Example 13 was swollen with hexane and filled in a glass column, and sodium sulfate (anhydrous) was layered thereon. The extract (mixture containing αHYA) obtained in Example 13 was suspended in an eluent of hexane:diethyl ether=8:2 and applied to the column. The eluate was flown at a flow rate of about 3 ml, and the solution discharged from the column was recovered in divided fractions. Each recovered fraction was analyzed by LC/MS and gas chromatography, unreacted substrate and fungus-derived lipid were removed. The eluent was changed to hexane:diethyl ether=6:4, and the fraction was further eluted. Each recovered fraction was analyzed by LC/MS and gas chromatography, and the fractions containing αHYA only were collected and concentrated in a rotary evaporator. A part of the obtained final product was methylesterified, and the purity of αHYA was evaluated by gas chromatography. As a result, αHYA having a purity of not less than 99% was obtained.

EXAMPLE 15

Production of αKetoA from αHYA by Using Anhydrous Chromic Acid ($CrO_3$)

To anhydrous chromic acid (2.67 g) were added sulfuric acid (2.3 ml) and water (7.7 ml), and acetone (90 ml) was added thereto to give a chromic acid solution. 2 g of αHYA and 40 ml of acetone were added into an Erlenmeyer flask, and the above-mentioned chromic acid solution was added drop by drop on ice while stirring the mixture with a stirrer. When the solution turned from blue to the color of powdered green tea, the dropwise addition of the chromic acid solution was stopped and the reaction was quenched with isopropyl alcohol. The precipitated sediment was filtered with a filter paper and placed in a partitioning funnel. Diethyl ether (150 ml) and Milli Q water (300 ml) were further added and the mixture was shaken well. The diethyl ether layer was washed several times with Milli Q water. To the diethyl ether layer after washing was added an appropriate amount of sodium sulfate (anhydrous), the mixture was stirred, and the residual water was removed. The anhydrous sodium sulfate added was filtered off with a filter paper, the obtained diethyl ether layer was concentrated in a rotary evaporator, and the reaction product and an unreacted substrate were extracted. Using a part of the extract, the purity of αKetoA was evaluated by LC/MS. As a result, about 80% of the extract was confirmed to be αKetoA.

EXAMPLE 16

Purification of αKetoA from Extract (Mixture Containing αKetoA) Obtained in Example 15

Silica gel (Wakogel® C-100) in a 20- to 30-fold weight that of the extract (mixture containing αKetoA) obtained in Example 15 was swollen with hexane and filled in a glass column, and sodium sulfate (anhydrous) was layered thereon. The extract (mixture containing αKetoA) obtained in Example 15 was suspended in an eluent of hexane:diethyl ether=8:2 and applied to the column. The eluent was flown at a flow rate of about 2 ml, and the solution discharged from the column was recovered in divided fractions. Each recovered fraction was analyzed by LC/MS and gas chromatography, and the fractions containing αKetoA only were collected and concentrated in a rotary evaporator. A part of the obtained final product was methylesterified, and the purity of αKetoA was evaluated by gas chromatography. As a result, αKetoA having a purity of not less than 98% was obtained.

EXAMPLE 17

Production of γHYA from γ-Linolenic Acid by Using Hydratase Expressed in *Escherichia coli*

Using hydratase-induced transformed *Escherichia coli*, a production test of γHYA from γ-linolenic acid was performed. The reaction mixture was 100 mM potassium phosphate buffer (pH 6.5) containing hydratase-induced transformed *Escherichia coli* (wet fungus weight 0.7 g), NADH (33 mg), FAD (0.8 mg), γ-linolenic acid (1 g) and BSA (0.2 g) and the total amount thereof was 10 ml. The reaction was performed by anaerobically shaking at 37° C., 225 rpm for 63 hr in the presence of an oxygen adsorbent Anaeropack (Mitsubishi Chemical Corporation). After the reaction, chloroform (10 ml) and methanol (10 ml) were added, the mixture was stirred, and the chloroform layer was recovered. Furthermore, chloroform (10 ml) was added to the residual solution, the mixture was stirred well, and the chloroform layer was recovered again. The recovered chloroform layers were collectively concentrated in a rotary evaporator, and the reaction product and an unreacted substrate were extracted. A part of the extract was methylesterified, and the purity of γHYA was evaluated by gas chromatography. As a result, about 85% of the extract was confirmed to be γHYA.

EXAMPLE 18

Purification of γHYA from Extract (Mixture Containing γHYA) Obtained in Example 17

Silica gel (Wakogel® C-100) in a 20- to 30-fold weight that of the extract (mixture containing γHYA) obtained in Example 17 was swollen with hexane and filled in a glass column, and sodium sulfate (anhydrous) was layered thereon. The extract (mixture containing γHYA) obtained in Example 17 was suspended in an eluent of hexane:diethyl ether=8:2 and applied to the column. The eluent was flown at a flow rate of about 3 ml, and the solution discharged from the column was recovered in divided fractions. Each recovered fraction was analyzed by LC/MS and gas chromatography, unreacted substrate and fungus-derived lipid were removed, the eluent was changed to hexane:diethyl ether=6:4, and the fraction was further eluted. Each recovered fraction was analyzed by LC/MS and gas chromatography, and the fractions containing γHYA only were collected and concentrated in a rotary evaporator. A part of the obtained final product was methylesterified, and the purity of γHYA was evaluated by gas chromatography. As a result, γHYA having a purity of not less than 99% was obtained.

EXAMPLE 19

Production of γKetoA from γHYA by Using Anhydrous Chromic Acid ($CrO_3$)

To anhydrous chromic acid (2.67 g) were added sulfuric acid (2.3 ml) and water (7.7 ml), and acetone (90 ml) was added thereto to give a chromic acid solution. 2 g of γHYA and 40 ml of acetone were added into an Erlenmeyer flask, and the above-mentioned chromic acid solution was added drop by drop on ice while stirring the mixture with a stirrer. When the solution turned from blue to the color of powdered green tea, the dropwise addition of the chromic acid solution was stopped and the reaction was quenched with isopropyl alcohol. The precipitated sediment was filtered with a filter paper and placed in a partitioning funnel. Diethyl ether (150 ml) and Milli Q water (300 ml) were further added and the mixture was shaken well. The diethyl ether layer was washed several times with Milli Q water. To the diethyl ether layer after washing was added an appropriate amount of sodium sulfate (anhydrous), the mixture was stirred, and the residual water was removed.

The anhydrous sodium sulfate added was filtered off with a filter paper, the obtained diethyl ether layer was concentrated in a rotary evaporator, and the reaction product and an unreacted substrate were extracted. Using a part of the extract, the purity of γKetoA was evaluated by LC/MS. As a result, about 95% of the extract was confirmed to be γKetoA.

EXAMPLE 20

Production of sHYA from Stearidonic Acid by Using Hydratase Expressed in *Escherichia coli*

Using hydratase-induced transformed *Escherichia coli*, a production test of sHYA from stearidonic acid was performed. The reaction mixture was 100 mM potassium phosphate buffer (pH 6.5) containing hydratase-induced transformed *Escherichia coli* (wet fungus weight 0.7 g), NADH (33 mg), FAD (0.8 mg), stearidonic acid (0.2 g) and BSA (40 mg) and the total amount thereof was 10 ml. The reaction was performed by anaerobically shaking at 37° C., 225 rpm for 63 hr in the presence of an oxygen adsorbent Anaeropack (Mitsubishi Chemical Corporation). After the reaction, chloroform (10 ml) and methanol (10 ml) were added to the reaction mixture (160 ml), the mixture was stirred, and the chloroform layer was recovered. Furthermore, chloroform (10 ml) was added to the residual solution, the mixture was stirred well, and the chloroform layer was recovered again. The recovered chloroform layers were collectively concentrated in a rotary evaporator, and the reaction product and an unreacted substrate were extracted. A part of the extract was methylesterified, and the purity of sHYA was evaluated by gas chromatography. As a result, about 50% of the extract was confirmed to be sHYA.

EXAMPLE 21

Production of 10,12-Dihydroxyoctadecanoic Acid (rHYA) from Ricinoleic Acid by Using Hydratase Expressed in *Escherichia coli*

Using hydratase-induced transformed *Escherichia coli*, a production test of rHYA from ricinoleic acid was performed. The reaction mixture was 100 mM potassium phosphate buffer (pH 6.5) containing hydratase-induced transformed *Escherichia coli* (wet fungus weight 0.7 g), NADH (33 mg), FAD (0.8 mg), ricinoleic acid (1 g) and BSA (0.2 g) and the total amount thereof was 10 ml. The reaction was performed by anaerobically shaking at 37° C., 225 rpm for 63 hr in the presence of an oxygen adsorbent Anaeropack (Mitsubishi Chemical Corporation). After the reaction, chloroform (10 ml) and methanol (10 ml) were added to the reaction mixture, the mixture was stirred, and the chloroform layer was recovered. Furthermore, chloroform (10 ml) was added to the residual solution, the mixture was stirred well, and the chloroform layer was recovered again. The recovered chloroform layers were collectively concentrated in a rotary evaporator, and the reaction product and an unreacted substrate were extracted. A part of the extract was methylesterified, and the purity of rHYA was evaluated by gas chromatography. As a result, about 95% of the extract was confirmed to be rHYA.

EXAMPLE 22

Production of KetoC from KetoA by Using Isomerase Expressed in *Escherichia coli*

KetoA (1 g), BSA (0.2 g) and 100 mM potassium phosphate buffer (pH 7.5, 4 ml) were emulsified by ultrasonication, and the emulsion was dispensed into 10 test tubes. To each test tube was added isomerase-expressing transformed *Escherichia coli*, suspended in 100 mM potassium phosphate buffer (pH 7.5) at 2 ml/g, to the total amount of 1 ml. The reaction was performed by anaerobically shaking at 37° C., 225 rpm for 15 hr in the presence of an oxygen adsorbent Anaeropack (Mitsubishi Chemical Corporation). After the reaction, 2 ml of methanol was added to each test tube, the mixture was stirred by Vortex and, after centrifugation, the supernatant was recovered. Furthermore, 2 ml of methanol was added to the residue, the mixture was stirred by Vortex and, after centrifugation, the supernatant was recovered again. The recovered supernatants were collectively concentrated in a rotary evaporator. 1 ml of distilled water and 3 ml of hexane were added to the concentrate, the mixture was stirred by Vortex, and the hexane layer was recovered after centrifugation. The reaction product and an unreacted substrate were extracted. Furthermore, 3 ml of hexane was added to the residual solution, the mixture was stirred well, and the hexane layer was recovered again after centrifugation. The recovered hexane layers were collectively concentrated in a rotary evaporator, and the reaction product and an unreacted substrate were extracted. A part of the extract was methylesterified, and the purity of KetoC was evaluated by gas chromatography. As a result, about 56% of the extract was confirmed to be KetoC.

EXAMPLE 23

Purification of KetoC by HPLC

Monitoring was performed by using Develosil C30-UG-3 manufactured by NOMURA CHEMICAL CO., LTD. (10× 150 mm), mobile phase of acetonitrile:water:acetic acid (80:20:0.002), flow rate 3.5 ml/min, column temperature 30° C., detection by absorption at 225 nm. The mixture obtained in the above-mentioned Example 24 was dissolved in methanol at 100 mg/ml, and 0.15 ml was applied to the column. Only the peak of KetoC eluted at retention time about 7.5 min was fractionated. The eluents in the fractionated solutions were collectively removed in an evaporator. A part of the obtained final product was methylesterified, and the purity of KetoC was evaluated by gas chromatography and LC/MS. As a result, KetoC was obtained at a purity of not less than 98%.

EXAMPLE 24

Production of αKetoC from αKetoA by Using Isomerase Expressed in *Escherichia coli*

αKetoA (0.5 g), BSA (0.1 g) and 100 mM potassium phosphate buffer (pH 7.5, 2 ml) were emulsified by ultrasonication, and the emulsion was dispensed into 4 test tubes. To each test tube was added isomerase-expressing transformed *Escherichia coli* (0.5 ml), suspended in 100 mM potassium phosphate buffer (pH 7.5) at 2 ml/g, to the total amount of 1 ml. The reaction was performed by anaerobically shaking at 37° C., 225 rpm for 15 hr in the presence of an oxygen adsorbent Anaeropack (Mitsubishi Chemical Corporation). After the reaction, 2 ml of methanol was added to each test tube, the mixture was stirred by Vortex and, after centrifugation, the supernatant was recovered. Furthermore, 2 ml of methanol was added to the residue, the mixture was stirred by Vortex and, after centrifugation, the supernatant was recovered again. The recovered supernatants were collectively concentrated in a rotary evaporator. 1 ml of distilled water and 3 ml of hexane were added to the concentrate, the mixture was stirred by Vortex, and the hexane layer was recovered after centrifugation. The reaction product and an unreacted substrate were extracted. Furthermore, 3 ml of hexane was added to the residual solution, the mixture was stirred well, and the hexane layer was recovered again after centrifugation. The recovered hexane layers were collectively concentrated in a rotary evaporator, and the reaction product and an unreacted substrate were extracted. Using a part of the extract, the purity of αKetoC was evaluated by high performance liquid chromatography. As a result, about 65% of the extract was confirmed to be αKetoC.

EXAMPLE 25

Purification of αKetoC by HPLC

Monitoring was performed by using Develosil C30-UG-5 manufactured by NOMURA CHEMICAL CO., LTD., mobile phase of acetonitrile:water:acetic acid (60:40:0.002), flow rate 10 ml/min, column temperature 30° C., detection by absorption at 210 nm and 233 nm. The mixture obtained in the above-mentioned Example 26 was dissolved in methanol at 100 mg/ml, and 0.17 ml was applied to the column. Only the peak of αKetoC eluted was fractionated by using recycling system. The eluents in the fractionated solutions were collectively removed in an evaporator. A part of the obtained final product was methylesterified, and the purity of αKetoC was evaluated by gas chromatography and LC/MS. As a result, αKetoC was obtained at a purity of not less than 98%.

EXAMPLE 26

Production of γKetoC from γKetoA by Using Isomerase Expressed in *Escherichia coli*

γKetoA (0.5 g), BSA (0.1 g) and 100 mM potassium phosphate buffer (pH 7.5, 2 ml) were emulsified by ultrasonication, and the emulsion was dispensed into 4 test tubes. To each test tube was added isomerase-expressing transformed *Escherichia coli* (each 0.5 ml), suspended in 100 mM potassium phosphate buffer (pH 7.5) at 2 ml/g, to the total amount of 1 ml. The reaction was performed by anaerobically shaking at 37° C., 225 rpm for 15 hr in the presence of an oxygen adsorbent Anaeropack (Mitsubishi Chemical Corporation). After the reaction, 2 ml of methanol was added to each test tube, the mixture was stirred by Vortex and, after centrifugation, the supernatant was recovered. Furthermore, 2 ml of methanol was added to the residue, the mixture was stirred by Vortex and, after centrifugation, the supernatant was recovered again. The recovered supernatants were collectively concentrated in a rotary evaporator. 1 ml of distilled water and 3 ml of hexane were added to the concentrate, the mixture was stirred by Vortex, and the hexane layer was recovered after centrifugation. The reaction product and an unreacted substrate were extracted. Furthermore, 3 ml of hexane was added to the residual solution, the mixture was stirred well, and the hexane layer was recovered again after centrifugation. The recovered hexane layers were collectively concentrated in a rotary evaporator, and the reaction product and an unreacted substrate were extracted. Using a part of the extract, the purity of γKetoC was evaluated by LC/MS. As a result, about 95% of the extract was confirmed to be γKetoC.

EXAMPLE 27

Purification of γKetoC by HPLC

Monitoring was performed by using Develosil C30-UG-5 manufactured by NOMURA CHEMICAL CO., LTD., mobile phase of acetonitrile:water:acetic acid (60:40:0.002), flow rate 10 ml/min, column temperature 30° C., detection by absorption at 210 nm and 233 nm. The mixture obtained in the above-mentioned Example 26 was dissolved in methanol at 100 mg/ml, and 0.17 ml was applied to the column. Only the peak of γKetoC eluted was fractionated by using recycling system. The eluents in the fractionated solutions were collectively removed in an evaporator. A part of the obtained final product was methylesterified, and the purity of γKetoC was evaluated by gas chromatography and LC/MS. As a result, γKetoC was obtained at a purity of not less than 96%.

EXAMPLE 28

Production of KetoC from KetoA by Using Isomerase Expressed in *Escherichia coli*

KetoA (1 g), BSA (0.2 g) and 100 mM potassium phosphate buffer (pH 7.5, 4 ml) were emulsified by ultrasonication, and the emulsion was dispensed into 10 test tubes. To each test tube was added isomerase-expressing transformed *Escherichia coli*, suspended in 100 mM potassium phosphate buffer (pH 7.5) at 2 ml/g, to the total amount of 1 ml. The reaction was performed by anaerobically shaking at 37° C., 225 rpm for 15 hr in the presence of an oxygen adsorbent Anaeropack (Mitsubishi Chemical Corporation). After the reaction, 2 ml of methanol was added to each test tube, the mixture was stirred by Vortex and, after centrifugation, the supernatant was recovered. Furthermore, 2 ml of methanol was added to the residue, the mixture was stirred by Vortex and, after centrifugation, the supernatant was recovered again. The recovered supernatants were collectively concentrated in a rotary evaporator. 1 ml of distilled water and 3 ml of hexane were added to the concentrate, the mixture was stirred by Vortex, and the hexane layer was recovered after centrifugation. The reaction product and an unreacted substrate were extracted. Furthermore, 3 ml of hexane was added to the residual solution, the mixture was stirred well, and the hexane layer was recovered again after centrifugation. The recovered hexane layers were collectively concentrated in a rotary evaporator, and the reaction product and an unreacted substrate were extracted. A part of the extract was methylesterified, and the purity of KetoC was evaluated by gas chromatography. As a result, about 56% of the extract was confirmed to be KetoC.

EXAMPLE 29

Purification of KetoC by HPLC

Monitoring was performed by using Develosil C30-UG-3 manufactured by NOMURA CHEMICAL CO., LTD. (10× 150 mm), mobile phase of acetonitrile:water:acetic acid (80:20:0.002), flow rate 3.5 ml/min, column temperature 30° C., detection by absorption at 225 nm. The mixture obtained in the above-mentioned Example 28 was dissolved in methanol at 100 mg/ml, and 0.15 ml was applied to the column. Only the peak of KetoC eluted at retention time about 7.5 min was fractionated. The eluents in the fractionated solutions were collectively removed in an evaporator. A part of the obtained final product was methylesterified, and the purity of KetoC was evaluated by gas chromatography and LC/MS. As a result, KetoC was obtained at a purity of not less than 98%.

EXAMPLE 30

Production of KetoB from KetoC by Using Saturase Expressed in *Escherichia coli*

Using saturase, a production test of KetoB was performed. The reaction mixture was 100 mM potassium phosphate buffer (pH 6.5) containing saturase-induced transformed *Escherichia coli* (wet fungus weight 33 mg), 0.5 mM NADH, 0.01 mM FAD, KetoC (5.2 mg) and 1 mg of BSA, and the total amount thereof was 1 ml. The reaction was performed by anaerobically shaking at 37° C., 200 rpm for 17 hr in the presence of an oxygen adsorbent Anaeropack (Mitsubishi Chemical Corporation). After the reaction, lipid was extracted from the reaction mixture by the Bligh-Dyer method and methylesterified, after which the production of KetoB was evaluated by gas chromatography. As a result, it was clarified that KetoB was produced at a conversion rate of 30%.

EXAMPLE 31

Production of αKetoB from αKetoA by Using Isomerase and Saturase Expressed in *Escherichia coli*

Using isomerase and saturase, a production test of αKetoB was performed. The reaction mixture was 100 mM potassium phosphate buffer (pH 7.5) containing isomerase-induced transformed *Escherichia coli* (wet fungus weight 80 mg), saturase-induced transformed *Escherichia coli* (wet fungus weight 80 mg), 0.5 mM NADH, 0.01 mM FAD, αKetoA (2 mg) and 0.4 mg BSA, and the total amount thereof was 1 ml. The reaction was performed by anaerobically shaking at 37° C., 225 rpm for 18 hr in the presence of an oxygen adsorbent Anaeropack (Mitsubishi Chemical Corporation). After the reaction, lipid was extracted from the reaction mixture by the Bligh-Dyer method and methylesterified, after which the production of αKetoB was evaluated by gas chromatography. As a result, it was clarified that αKetoB was produced at a conversion rate of 99%.

EXAMPLE 32

Production of HYC from KetoC by Using Dehydrogenase Expressed in *Escherichia coli*

Using the purified dehydrogenase obtained in Example 6, a production test of HYC was performed. The reaction mixture was 20 mM potassium phosphate buffer (pH 6.5) containing purified dehydrogenase (enzyme content 83 μg), 0.5 mM NADH, 0.01 mM FAD and 0.005% KetoC and the total amount thereof was 0.8 ml. The reaction was performed by anaerobically shaking at 37° C., 120 rpm for 4 hr in the presence of an oxygen adsorbent Anaeropack (Mitsubishi Chemical Corporation). After the reaction, lipid was extracted from the reaction mixture by the Bligh-Dyer method and methylesterified, after which the production of HYC was evaluated by gas chromatography. As a result, production of HYC (0.02 mg) from KetoC was confirmed.

EXAMPLE 33

Production of HYB from KetoB by Using Dehydrogenase Expressed in *Escherichia coli*

Using dehydrogenase, a production test of HYB was performed. The reaction mixture was 20 mM potassium phosphate buffer (pH 6.5) containing dehydrogenase-induced transformed *Escherichia coli* (wet fungus weight 50 mg), 0.5 mM NADH, 0.01 mM FAD and 0.02% KetoB and the total amount thereof was 1 ml. The reaction was performed by anaerobically shaking at 37° C., 120 rpm for 4 hr in the presence of an oxygen adsorbent Anaeropack (Mitsubishi Chemical Corporation). After the reaction, lipid was extracted from the reaction mixture by the Bligh-Dyer method and methylesterified, after which the production of HYB was evaluated by gas chromatography. As a result, production of HYB (0.08 mg) from KetoB was confirmed.

EXAMPLE 34

Production of CLA1 and CLA2 from HYC by Using Dehydrase Expressed in *Escherichia coli*

Using the purified dehydrase obtained in Example 5, a production test of CLA1 and CLA2 was performed. The reaction mixture was 20 mM potassium phosphate buffer (pH 6.5) containing purified dehydrase (enzyme content 300 μg), 0.5 mM NADH, 0.01 mM FAD and 0.035% HYC and the total amount thereof was 0.8 ml. The reaction was performed by anaerobically shaking at 37° C., 120 rpm for 4 hr in the presence of an oxygen adsorbent Anaeropack (Mitsubishi Chemical Corporation). After the reaction, lipid was extracted from the reaction mixture by the Bligh-Dyer method and methylesterified, after which the production of CLA1 and CLA2 was evaluated by gas chromatography. As a result, production of CLA1 (0.05 mg) and CLA2 (0.15 mg) from HYC was confirmed.

EXAMPLE 35

Production of Oleic Acid and Trans-10-Octadecenoic Acid from HYB by Using Dehydrase Expressed in *Escherichia coli*

Using dehydrase, a production test of oleic acid and trans-10-octadecenoic acid was performed. The reaction mixture was 20 mM potassium phosphate buffer (pH 6.5) containing dehydrase-induced transformed *Escherichia coli* (wet fungus 50 mg), 0.5 mM NADH, 0.01 mM FAD and 0.2% HYB and the total amount thereof was 1 ml. The reaction was performed by anaerobically shaking at 37° C., 120 rpm for 4 hr in the presence of an oxygen adsorbent Anaeropack (Mitsubishi Chemical Corporation). After the reaction, lipid was extracted from the reaction mixture by the Bligh-Dyer method and methylesterified, after which the production of oleic acid and trans-10-octadecenoic acid was evaluated by gas chromatography. As a result, production of oleic acid (0.02 mg) and trans-10-octadecenoic acid (0.1 mg) from HYB was confirmed.

EXAMPLE 36

Production of Linoleic Acid and CLA3 from HYA by Using Dehydrase Expressed in *Escherichia coli*

Using dehydrase, a production test of linoleic acid and trans-10,cis-12-CLA was performed. The reaction mixture was 20 mM potassium phosphate buffer (pH 6.5) containing dehydrogenase-induced transformed *Escherichia coli* (wet fungus 50 mg), 0.5 mM NADH, 0.01 mM FAD and 0.07% HYA and the total amount thereof was 1 ml. The reaction was performed by anaerobically shaking at 37° C., 120 rpm for 4 hr in the presence of an oxygen adsorbent Anaeropack (Mitsubishi Chemical Corporation). After the reaction, lipid was extracted from the reaction mixture by the Bligh-Dyer method and methylesterified, after which the production of linoleic acid and CLA3 was evaluated by gas chromatography. As a result, production of linoleic acid (0.26 mg) and trans-10,cis-12-CLA (0.07 mg) from HYA was confirmed.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

This application is based on a patent application No. 2012-108928 filed in Japan (filing date: May 10, 2012), the contents of which are incorporated in full herein.

INDUSTRIAL APPLICABILITY

According to the method of the present invention, since various oxo fatty acids can be produced efficiently, the oxo fatty acids can be applied to various fields such as medicament, food and the like. According to the method of the present invention, moreover, various rare fatty acids can be produced from oxo fatty acid as a starting material, which is extremely useful.

---

The invention claimed is:

1. A method of producing an oxo fatty acid having 18 carbon atoms and a carbonyl group at the 10-position, and not having a double bond at the 11- and 12-positions comprising contacting an oxo fatty acid having 18 carbon atoms, a carbonyl group at the 10-position and a trans-type double bond at the 11-position and a saturase to form an oxo fatty acid having 18 carbon atoms and a carbonyl group at the 10-position, and not having a double bond at the 11- and 12-positions, wherein the saturase is
  (i) obtained from Lactobacillus plantarum FERM BP-10549 strain, or
  (ii) an enzyme protein of any of the following (a) - (c):
    (a) a protein consisting of the amino acid sequence shown in SEQ ID NO: 2,
    (b) a protein comprising the amino acid sequence shown in SEQ ID NO: 2, wherein 1-20 amino acids are deleted, substituted, inserted, and/or added, and having an enzyme activity of catalyzing the saturation reaction, or
    (c) a protein encoded by a nucleotide sequence that hybridizes to the complement of the nucleotide sequence shown in SEQ ID NO: 1 under conditions of washing 2-3 times with a buffer comprising 0.1× SSC and 0.1% SDS at 68° C., and having an enzyme activity to catalyze the saturation reaction.

2. The method according to claim 1, wherein the oxo fatty acid having 18 carbon atoms, a carbonyl group at the 10-position and a trans-type double bond at the 11-position is 10-oxo-trans-11-octadecenoic acid, 10-oxo-cis-6,trans-11,-octadecadienoic acid, 10-oxo-trans-11,cis-15-octadecadienoic acid or 10-oxo-cis-6,trans-11,cis-15-octadecatrienoic acid.

3. The method according to claim 1, wherein the saturase is obtained from Lactobacillus plantarum FERM BP-10549 strain.

4. The method according to claim 1, wherein the saturase is an enzyme protein of any of the following (a) - (c):
   (a) a protein consisting of the amino acid sequence shown in SEQ ID NO: 2,
   (b) a protein comprising the amino acid sequence shown in SEQ ID NO: 2, wherein 1-20 amino acids are deleted, substituted, inserted, and/or added, and having an enzyme activity of catalyzing the saturation reaction, or
   (c) a protein encoded by a nucleotide sequence that hybridizes to the complement of the nucleotide sequence shown in SEQ ID NO: 1 under conditions of washing 2-3 times with a buffer comprising 0.1×SSC and 0.1% SDS at 68° C., and having an enzyme activity to catalyze the saturation reaction in claim 1.

5. The method according to claim 1, wherein the saturase is an enzyme protein consisting of the amino acid sequence shown in SEQ ID NO: 2.

6. The method according to claim 1, wherein the saturase is a protein comprising the amino acid sequence shown in SEQ ID NO: 2, wherein 1-20 amino acids are deleted, substituted, inserted, and/or added, and having an enzyme activity of catalyzing the saturation reaction.

7. The method according to claim 1, wherein the saturase is a protein comprising an amino acid sequence shown in SEQ ID NO: 2, wherein 1-10 amino acids are deleted, substituted, inserted, and/or added, and having an enzyme activity of catalyzing the saturation reaction.

8. The method according to claim 4, wherein the saturase is a protein encoded by a nucleotide sequence that hybridizes to the complement of the nucleotide sequence shown in SEQ ID NO: 1 under conditions of washing 2-3 times with a buffer comprising 0.1×SSC and 0.1% SDS at 68° C., and having an enzyme activity to catalyze the saturation reaction.

* * * * *

SEQUENCE LISTING

<160> NUMBER OF SEQ ID NOS: 6

<210> SEQ ID NO 1
<211> LENGTH: 654
<212> TYPE: DNA
<213> ORGANISM: Lactobacillus plantarum
<220> FEATURE:
<221> NAME/KEY: CDS
<222> LOCATION: (1)..(654)

<400> SEQUENCE: 1

```
atg tca gaa gca gtg aaa aat ttg gtg aac aat gat tta gca gac gtg      48
Met Ser Glu Ala Val Lys Asn Leu Val Asn Asn Asp Leu Ala Asp Val
1               5                   10                  15 atg ttt aac cgc cat tca gtt cgg cag ttt gac ccg aac gtt aaa att      96
Met Phe Asn Arg His Ser Val Arg Gln Phe Asp Pro Asn Val Lys Ile
                20                  25                  30 gga cgt gat gag tta caa aag atg att gcg gaa gca gcc acc gcg cca     144
Gly Arg Asp Glu Leu Gln Lys Met Ile Ala Glu Ala Ala Thr Ala Pro
            35                  40                  45 tcg gca tgt aat tta cag tca tgg cac ttt gtc gtc gtg gat acc ccc     192
Ser Ala Cys Asn Leu Gln Ser Trp His Phe Val Val Val Asp Thr Pro
        50                  55                  60
```

```
gag gca aag gct aag ttc aaa caa gcc gtg atg aaa ttc aac tac cca        240
Glu Ala Lys Ala Lys Phe Lys Gln Ala Val Met Lys Phe Asn Tyr Pro
 65                  70                  75                  80 cag gtc gac agt gca tcg gcc atc gtc ttt att gcc ggt gac acc cag        288
Gln Val Asp Ser Ala Ser Ala Ile Val Phe Ile Ala Gly Asp Thr Gln
                 85                  90                  95 tcg cat tat gtt tat cgc gat gtc tgg aac aaa gtt tat gag gat ggg        336
Ser His Tyr Val Tyr Arg Asp Val Trp Asn Lys Val Tyr Glu Asp Gly
            100                 105                 110 aat att acg aag gaa cgc ttg gat cag att ctg gga acc ttc tta cca        384
Asn Ile Thr Lys Glu Arg Leu Asp Gln Ile Leu Gly Thr Phe Leu Pro
        115                 120                 125 tta tat gaa aat gcc aca cca gat ttc ttg aaa ttc gat gcg acg att        432
Leu Tyr Glu Asn Ala Thr Pro Asp Phe Leu Lys Phe Asp Ala Thr Ile
    130                 135                 140 gat tgt tcc gtt gtc ggg atg cag ttg ctg cta gtg gca cgg gct cat        480
Asp Cys Ser Val Val Gly Met Gln Leu Leu Leu Val Ala Arg Ala His
145                 150                 155                 160 ggg tat gat gcc aat gcg ttc tcc gga att gac ttt gaa aag atg att        528
Gly Tyr Asp Ala Asn Ala Phe Ser Gly Ile Asp Phe Glu Lys Met Ile
                165                 170                 175 ccg acg ctg ggt ctt gat cct aaa cga tac gtg cca gta atg ggg atc        576
Pro Thr Leu Gly Leu Asp Pro Lys Arg Tyr Val Pro Val Met Gly Ile
            180                 185                 190 gca atc ggg aaa gca gcg caa gaa ccg ctc cat acg act cgg tac gat        624
Ala Ile Gly Lys Ala Ala Gln Glu Pro Leu His Thr Thr Arg Tyr Asp
        195                 200                 205 gcc aaa aca cag act gat ttc tta gcc taa                                654
Ala Lys Thr Gln Thr Asp Phe Leu Ala
    210                 215

<210> SEQ ID NO 2
<211> LENGTH: 217
<212> TYPE: PRT
<213> ORGANISM: Lactobacillus plantarum

<400> SEQUENCE: 2

Met Ser Glu Ala Val Lys Asn Leu Val Asn Asn Asp Leu Ala Asp Val
 1               5                  10                  15

Met Phe Asn Arg His Ser Val Arg Gln Phe Asp Pro Asn Val Lys Ile
                20                  25                  30

Gly Arg Asp Glu Leu Gln Lys Met Ile Ala Glu Ala Ala Thr Ala Pro
            35                  40                  45

Ser Ala Cys Asn Leu Gln Ser Trp His Phe Val Val Asp Thr Pro
        50                  55                  60

Glu Ala Lys Ala Lys Phe Lys Gln Ala Val Met Lys Phe Asn Tyr Pro
 65                  70                  75                  80

Gln Val Asp Ser Ala Ser Ala Ile Val Phe Ile Ala Gly Asp Thr Gln
                 85                  90                  95

Ser His Tyr Val Tyr Arg Asp Val Trp Asn Lys Val Tyr Glu Asp Gly
            100                 105                 110

Asn Ile Thr Lys Glu Arg Leu Asp Gln Ile Leu Gly Thr Phe Leu Pro
        115                 120                 125

Leu Tyr Glu Asn Ala Thr Pro Asp Phe Leu Lys Phe Asp Ala Thr Ile
    130                 135                 140

Asp Cys Ser Val Val Gly Met Gln Leu Leu Leu Val Ala Arg Ala His
145                 150                 155                 160

Gly Tyr Asp Ala Asn Ala Phe Ser Gly Ile Asp Phe Glu Lys Met Ile
```

```
                         165                 170                 175
Pro Thr Leu Gly Leu Asp Pro Lys Arg Tyr Val Pro Val Met Gly Ile
            180                 185                 190

Ala Ile Gly Lys Ala Ala Gln Glu Pro Leu His Thr Thr Arg Tyr Asp
        195                 200                 205

Ala Lys Thr Gln Thr Asp Phe Leu Ala
    210                 215
```

```
<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ggcggattac gaaagcgagg                                                    20

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
gagcgggaat cccgctctt                                                     19

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
caccatgtca gaagcagtga aaa                                                23

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
ggctaagaaa tcagtctgtg ttttgg                                             26
```